(12) United States Patent
Starke et al.

(10) Patent No.: US 6,906,058 B2
(45) Date of Patent: Jun. 14, 2005

(54) 1,5-BENZOTHIAZEPINES AND THEIR USE AS HYPOLIPIDAEMICS

(75) Inventors: Ingemar Starke, Mölndal (SE); Mickael Dahlström, Mölndal (SE); David Blomberg, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/220,877

(22) PCT Filed: Mar. 5, 2001

(86) PCT No.: PCT/GB01/00909

§ 371 (c)(1), (2), (4) Date: Sep. 6, 2002

(87) PCT Pub. No.: WO01/66533

PCT Pub. Date: Sep. 13, 2001

(65) Prior Publication Data

US 2003/0166927 A1 Sep. 4, 2003

(30) Foreign Application Priority Data

Mar. 8, 2000 (SE) ............................................. 0000772

(51) Int. Cl.⁷ .................... C07D 281/10; C07D 401/12; A61K 31/554; A61K 31/662; A61P 3/06
(52) U.S. Cl. .................................... 514/211.1; 540/552
(58) Field of Search ........................ 540/552; 514/211.1

(56) References Cited

FOREIGN PATENT DOCUMENTS

| | | |
|---|---|---|
| DE | 19825804 | 12/1999 |
| EP | 0 864 582 | 9/1998 |
| WO | 93/16055 | 8/1993 |
| WO | 94/18183 | 8/1994 |
| WO | 94/18184 | 8/1994 |
| WO | 96/05188 | 2/1996 |
| WO | 96/08484 | 3/1996 |
| WO | 96/16051 A | 5/1996 |
| WO | 97/33882 | 9/1997 |
| WO | 98/38182 | 9/1998 |
| WO | 98/40375 | 9/1998 |
| WO | 99/34278 | 7/1999 |
| WO | 99/35135 A | 7/1999 |
| WO | 99/64409 | 12/1999 |
| WO | 99/64410 | 12/1999 |
| WO | 00/01687 | 1/2000 |
| WO | 00/38725 | 7/2000 |
| WO | 00/38726 | 7/2000 |
| WO | 00/38727 | 7/2000 |
| WO | 00/38728 | 7/2000 |
| WO | 00/38729 | 7/2000 |
| WO | 00/47568 | 8/2000 |
| WO | 00/61568 | 10/2000 |
| WO | 00/62810 | 10/2000 |
| WO | 01/60807 A1 | 8/2001 |
| WO | 01/68096 A2 | 9/2001 |
| WO | 01/68637 A2 | 9/2001 |
| WO | 02/08211 A2 | 1/2002 |
| WO | 02/32428 A2 | 4/2002 |
| WO | 02/50051 A1 | 6/2002 |
| WO | 03/020710 A1 | 3/2003 |
| WO | 03/022286 A1 | 3/2003 |
| WO | 03/022825 A1 | 3/2003 |
| WO | 03/022830 A1 | 3/2003 |

*Primary Examiner*—Bruck Kifle
(74) *Attorney, Agent, or Firm*—Morgan, Lewis & Bockius LLP

(57) ABSTRACT

The present invention relates to compounds of formula (I) wherein $R^1$ and $R^2$ are independently selected from $C_{1-6}$alkyl; one of $R^4$ and $R^5$ is a group of formula (IA): $R^3$, $R^6$, $R^7$, $R^8$, $R^9$, $R^{10}$ and $R^{11}$ and the other of $R^4$ and $R^5$ are as defined within, pharmaceutically acceptable salts, solvates, solvates of such salts and prodrugs thereof and there use as ileal bile acid transport (IBAT) inhibitors for the treatment of hyperlipidaemia. Processes for their manufacture and pharmaceutical compositions containing them are also described.

12 Claims, No Drawings

1,5-BENZOTHIAZEPINES AND THEIR USE AS HYPOLIPIDAEMICS

This invention relates to benzothiazepine derivatives, or pharmaceutically acceptable salts, solvates, solvates of such salts and prodrugs thereof. These benzothiazepines possess ileal bile acid transport (IBAT) inhibitory activity and accordingly have value in the treatment of disease states associated with hyperlipidaemic conditions and they are useful in methods of treatment of a warm-blooded animal, such as man. The invention also relates to processes for the manufacture of said benzothiazepine derivatives, to pharmaceutical compositions containing them and to their use in the manufacture of medicaments to inhibit IBAT in a warm-blooded animal, such as man.

It is well-known that hyperlipidaemic conditions associated with elevated concentrations of total cholesterol and low-density lipoprotein cholesterol are major risk factors for cardiovascular atherosclerotic disease (for instance "Coronary Heart Disease: Reducing the Risk; a Worldwide View" Assman G., Carmena R. Cullen P. et al; Circulation 1999, 100, 1930–1938 and "diabetes and Cardiovascular Disease: A Statement for Healthcare Professionals from the American Heart Association" Grundy S, Benjamin I., Burke G., et al; Circulation, 1999, 100, 1134–46). Interfering with the circulation of bile acids within the lumen of the intestinal tracts is found to reduce the level of cholesterol. Previous established therapies to reduce the concentration of cholesterol involve, for instance, treatment with HMG-CoA reductase inhibitors, preferably statins such as simvastatin and fluvastatin, or treatment with bile acid binders, such as resins. Frequently used bile acid binders are for instance cholestyramine and cholestipol. One recently proposed therapy ("Bile Acids and Lipoprotein Metabolism: a Renaissance for Bile Acids in the Post Statin Era" Angelin B, Eriksson M, Rudling M; Current Opinion on Lipidology, 1999, 10, 269–74) involved the treatment with substances with an IBAT inhibitory effect.

Re-absorption of bile acid from the gastro-intestinal tract is a normal physiological process which mainly takes place in the ileum by the IBAT mechanism. Inhibitors of BAT can be used in the treatment of hypercholesterolaemia (see for instance "Interaction of bile acids and cholesterol with nonsystemic agents having hypocholesterolaemic properties", Biochemica et Biophysica Acta, 1210 (1994) 255–287). Thus, suitable compounds having such inhibitory IBAT activity are also useful in the treatment of hyperlipidaemic conditions. Substituted benzothiazepines possessing such IBAT inhibitory activity have been described, see for instance hypolipidaemic benzothiazepine compounds described in WO 93/16055, WO 94/18183, WO 94/18184, WO 96/05188, WO 96/08484, WO 96/16051, WO 97/33882, WO 98/38182, WO 99/35135, WO 98/40375 and EP 0 864 582.

The present invention is based on the discovery that certain benzothiazepine compounds surprisingly inhibit IBAT and that they posses characteristics that make them particularly suitable as medicaments. Such properties are expected to be of value in the treatment of disease states associated with hyperlipidaemic conditions.

Accordingly, the present invention provides a compound of formula (I):

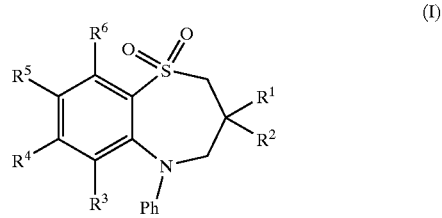

(I)

wherein:
$R^1$ and $R^2$ are independently selected from $C_{1-6}$alkyl;
one of $R^4$ and $R^5$ is a group of formula (IA):

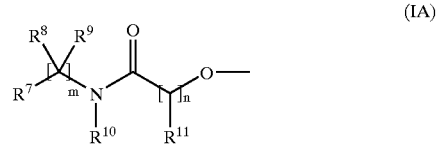

(IA)

$R^3$ and $R^6$ and the other of $R^4$ and $R^5$ are independently selected from hydrogen, halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N-($C_{1-4}$alkyl)amino, N,N-($C_{1-4}$alkyl)$_2$amino, $C_{1-4}$alkanoylamino, N-($C_{1-4}$alkyl)carbamoyl, N,N-($C_{1-4}$alkyl)$_2$carbamoyl, $C_{1-4}$alkylS(O)$_a$ wherein a is 0 to 2, $C_{1-4}$alkoxycarbonyl, N-($C_{1-4}$alkyl)sulphamoyl and N,N-($C_{1-4}$alkyl)$_2$sulphamoyl; wherein $R^3$ and $R^6$ and the other of $R^4$ and $R^5$ may be optionally substituted on carbon by one or more $R^{14}$;
$R^7$ is carboxy, sulpho, sulphino, phosphono, —P(O)(OR$^a$)(OR$^b$), P(O)(OH)(OR$^a$), —P(O)(OH)(R$^a$) or P(O)(OR$^a$)(R$^b$), wherein R$^a$, R$^b$, are independently selected from $C_{1-6}$alkyl; or $R^7$ is a group of formula (IB):

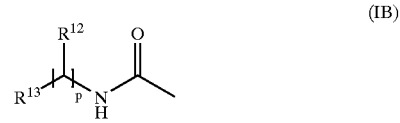

(IB)

$R^8$ and $R^9$ are independently hydrogen, $C_{1-4}$alkyl or a saturated cyclic group, or $R^8$ and $R^9$ together form $C_{2-6}$alkylene; wherein $R^8$ and $R^9$ or $R^8$ and $R^9$ together may be independently optionally substituted on carbon by one or more substituents selected from $R^{15}$; and wherein if said saturated cyclic group contains an —NH— moiety, that nitrogen may be optionally substituted by one or more $R^{20}$;
$R^{10}$ is hydrogen or $C_{1-4}$alkyl; wherein $R^{10}$ is optionally substituted on carbon by one or more substituents selected from $R^{24}$;
$R^{11}$ is hydrogen, $C_{1-4}$alkyl, carbocyclyl or heterocyclyl; wherein $R^{11}$ is optionally substituted on carbon by one or more substituents selected from $R^{16}$; and wherein if said heterocyclyl contains an —NH— moiety, that nitrogen may be optionally substituted by one or more $R^{21}$;
$R^{12}$ is hydrogen or $C_{1-4}$alkyl, carbocyclyl or heterocyclyl; wherein $R^{12}$ is optionally substituted on carbon by one or more substituents selected from $R^{17}$; and wherein if said heterocyclyl contains an —NH— moiety, that nitrogen may be optionally substituted by one or more $R^{22}$;
$R^{13}$ is carboxy, sulpho, sulphino, phosphono, —P(O)(OR$^c$)(OR$^d$), —P(O)(OH)(OR$^c$), —P(O)(OH)(R$^c$) or —P(O)(OR$^c$)(R$^d$) wherein R$^c$ and R$^d$ are independently selected from $C_{6-4}$alkyl;

m is 1–3; wherein the values of $R^8$ and $R^9$ may be the same or different;

n is 1–3; wherein the values of $R^{11}$ may be the same or different;

p is 1–3; wherein the values of $R^{12}$ may be the same or different;

$R^{14}$ and $R^{16}$ are independently selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N-($C_{1-4}$alkyl) amino, N,N-($C_{1-4}$alkyl)$_2$amino, $C_{1-4}$alkanoylamino, N-($C_{1-4}$ alkyl)carbamoyl, N,N-($C_{1-4}$alkyl)$_2$carbamoyl, $C_{1-4}$alkylS (O)$_a$ wherein a is 0 to 2, $C_{1-4}$alkoxycarbonyl, N-($C_{1-4}$alkyl) sulphamoyl and N,N-($C_{1-4}$alkyl)$_2$sulphamoyl; wherein $R^{14}$ and $R^{16}$ may be independently optionally substituted on carbon by one or more $R^{18}$;

$R^{15}$ and $R^{17}$ are independently selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N-($C_{1-4}$alkyl) amino, N,N-($C_{1-4}$alkyl)$_2$amino, $C_{1-4}$alkanoylamino, N-($C_{1-4}$ alkyl)carbamoyl, N,N-($C_{1-4}$alkyl)$_2$carbamoyl, $C_{1-4}$alkylS (O)$_a$ wherein a is 0 to 2, $C_{1-4}$alkoxycarbonyl, N-($C_{1-4}$alkyl) sulphamoyl and N,N-($C_{1-4}$alkyl)$_2$sulphamoyl, carbocyclyl, heterocyclyl, sulpho, sulphino, amidino, phosphono, —P(O) (OR$^e$)(OR$^f$), —P(O)(OH)(OR$^e$), —P(O)(OH)(R$^e$) or —P(O) (OR$^e$)(R$^f$), wherein R$^e$ and R$^f$ are independently selected from $C_{1-6}$alkyl; wherein $R^{15}$ and $R^{17}$ may be independently optionally substituted on carbon by one or more $R^{19}$; and wherein if said heterocyclyl contains an —NH— moiety, that nitrogen may be optionally substituted by one or more $R^{23}$;

$R^{18}$, $R^{19}$ and $R^{25}$ are independently selected from halo, hydroxy, cyano, carbamoyl, ureido, amino, nitro, carboxy, carbamoyl, mercapto, sulphamoyl, trifluoromethyl, trifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl;

$R^{20}$, $R^{21}$, $R^{22}$, $R^{23}$ and $R^{26}$ are independently $C_{1-4}$alkyl, $C_4$alkanoyl, $C_{1-4}$alkylsulphonyl, sulphamoyl, N-($C_{1-4}$alkyl) sulphamoyl, N,N-($C_{1-4}$alkyl)$_2$sulphamoyl, $C_{1-4}$alkoxycarbonyl, carbamoyl, N-($C_{1-4}$alkyl)carbamoyl, N,N-($C_{1-4}$alkyl)$_2$carbamoyl, benzyl, phenethyl, benzoyl, phenylsulphonyl and phenyl;

$R^{24}$ is selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N-($C_{1-4}$alkyl)amino, N)N-($C_{1-4}$alkyl)$_2$ amino, $C_{1-4}$alkanoylamino, N-($C_{1-4}$alkyl)carbamoyl, N,N-($C_{1-4}$alkyl)$_2$carbamoyl, $C_{1-4}$alkylS(O)$_a$ wherein a is 0 to 2, $C_{1-4}$alkoxycarbonyl, N-($C_{1-4}$alkyl)sulphamoyl and N,N-($C_{1-4}$ allyl)$_2$sulphamoyl, carbocyclyl, heterocyclyl; wherein $R^{24}$ may be independently optionally substituted on carbon by one or more $R^{25}$; and wherein if said heterocyclyl contains an —NH— moiety, that nitrogen may be optionally substituted by one or more $R^{26}$;

or a pharmaceutically acceptable salt, solvate, solvate of such a salt or a prodrug thereof.

In this specification the term "alkyl" includes both straight and branched chain alkyl groups but references to individual alkyl groups such as "propyl" are specific for the straight chain version only. For example, "$C_{1-6}$alkyl" includes $C_{1-4}$alkyl, $C_{1-3}$alkyl, propyl, isopropyl and t-butyl. However, references to individual alkyl groups such as 'propyl' are specific for the straight chained version only and references to individual branched chain alkyl groups such as 'isopropyl' are specific for the branched chain version only. A similar convention applies to other radicals, for example "phenyl$C_{1-6}$alkyl" would include phenyl$C_{1-4}$alkyl, benzyl, 1-phenylethyl and 2-phenylethyl. The term "halo" refers to fluoro, fluoro, bromo and iodo. For the avoidance of doubt where m>1 the values of $R^8$ may be the same or different.

Where optional substituents are chosen from "one or more" groups it is to be understood that this definition includes all substituents being chosen from one of the specified groups or the substituents being chosen from two or more of the specified groups.

A "saturated cyclic group" is a totally or partially saturated, mono or bicyclic ring containing 3–12 atoms of which 0–4 atoms are chosen from nitrogen, sulphur or oxygen, which may, unless otherwise specified, be carbon or nitrogen linked. Preferably "saturated cyclic group" refers to a totally saturated, monocyclic ring containing 5 or 6 atoms or a totally saturated bicyclic ring containing 9 or 10 atoms of which 0–4 atoms are chosen from nitrogen, sulphur or oxygen, which may, unless otherwise specified, be carbon or nitrogen linked. Examples and suitable values of the term "saturated cyclic group" are cyclohexyl, cyclopropyl, pyrrolidinyl, morpholino and piperidyl. Preferably "saturated cyclic group" is cyclohexyl.

A "heterocyclyl" is a saturated, partially saturated or unsaturated, mono or bicyclic ring containing 3–12 atoms of which at least one atom is chosen from nitrogen, sulphur or oxygen, which may, unless otherwise specified, be carbon or nitrogen linked, wherein a —CH$_2$— group can optionally be replaced by a —C(O)— or a ring sulphur atom may be optionally oxidised to form the S-oxides. Preferably a "heterocyclyl" is a saturated, partially saturated or unsaturated, mono or bicyclic ring containing 5 or 6 atoms of which at least one atom is chosen from nitrogen, sulphur or oxygen, which may, unless otherwise specified, be carbon or nitrogen linked, wherein a —CH$_2$— group can optionally be replaced by a —C(O)— or a ring sulphur atom may be optionally oxidised to form S-oxide(s). Examples and suitable values of the term "heterocyclyl" are thiazolidinyl, pyrrolidinyl, pyrrolinyl, 2-pyrrolidonyl, 2,5-dioxopyrrolidinyl, 2-benzoxazolinonyl, 1,1-dioxotetrahydrothienyl, 2,4dioxoimidazolidinyl, 2-oxo-1,3,4-(4-triazolinyl), 2-oxazolidinonyl, 5,6-dihydrouracilyl, 1,3-benzodioxolyl, 1,2,4oxadiazolyl, 2-azabicyclo[2.2.1]heptyl, 4-thiazolidonyl, morpholino, 2-oxotetrahydrofuranyl, tetrahydrofliranyl, 2,3-dihydrobenzofuranyl, benzothienyl, tetrahydropyranyl, piperidyl, 1-oxo-1,3-dihydroisoindolyl, piperazinyl, thiomorpholino, 1,1-dioxothiomorpholino, tetrahydropyranyl, 1,3-dioxolanyl, homopiperazinyl, thienyl, isoxazolyl, imidazolyl, pyrrolyl, thiadiazolyl, isothiazolyl, 1,2,4-triazolyl, 1,3,4-triazolyl, pyranyl, indolyl, pyrimidyl, thiazolyl, pyrazinyl, pyridazinyl, pyridyl, 4-pyridonyl, quinolyl and 1-isoquinolonyl.

A "carbocyclyl" is a saturated, partially saturated or unsaturated, mono or bicyclic carbon ring that contains 3–12 atoms; wherein a —CH$_2$— group can optionally be replaced by a —C(O)—. Preferably "carbocycly" is a monocyclic ring containing 5 or 6 atoms or a bicyclic ring containing 9 or 10 atoms. Suitable values for "carbocyclyl" include cyclopropyl, cyclobutyl, 1-oxocyclopentyl, cyclopentyl, cyclopentenyl, cyclohexyl, cyclohexenyl, phenyl, naphthyl, tetralinyl, indanyl or 1-oxoindanyl. Particularly "carbocyclyl" is cyclopropyl, cyclobutyl, 1-oxocyclopentyl, cyclopentyl, cyclopentenyl, cyclohexyl, cyclohexenyl, phenyl or 1-oxoindanyl.

An example of "$C_{1-4}$alkanoyloxy" is acetoxy. Examples of "$C_{1-4}$alkoxycarbonyl" include methoxycarbonyl, ethoxycarbonyl, n- and t-butoxycarbonyl. Examples of "$C_{1-4}$alkoxy" include methoxy, ethoxy and propoxy. Examples of "$C_{1-4}$alkanoylamino" include formamido, acetamido and propionylamino. Examples of "$C_{1-4}$alkylS(O)_a$ wherein a is 0 to 2" include methylthio, ethylthio, methylsulphinyl, ethylsulphinyl, mesyl and ethylsulphonyl. Examples of "$C_{1-4}$alkylsulphanyl" are methyl thio and ethylthio. Examples of "$C_{1-4}$alkanoyl" include $C_{1-3}$alkanoyl, propionyl and acetyl. Examples of "N-$C_{1-4}$alkylamino" include methylamino and ethylamino. Examples of "N,N-($C_{1-4}$alkyl)_2$amino" include di-N-methylamino, di-(N-ethyl)amino and N-ethyl-N-methylamino. Examples of "$C_{2-4}$alkenyl" are vinyl, allyl and 1-propenyl. Examples of "$C_{2-4}$alkynyl" are ethynyl, 1-propynyl and 2-propynyl. Examples of "N-($C_{1-4}$alkyl)sulphamoyl" are N-($C_{1-3}$alkyl)sulphamoyl, N-(methyl)sulphamoyl and N-(ethyl)sulphamoyl. Examples of "N-($C_{1-4}$alkyl)_2$sulphamoyl" are N,N-(dimethyl)sulphamoyl and N-(methyl)-N-(ethyl)sulphamoyl. Examples of "N-($C_{1-4}$alkyl)carbamoyl" are methylaminocarbonyl and ethylaminocarbonyl. Examples of "N,N-($C_{1-4}$allyl)_2$carbamoyl" are dimethylaminocarbonyl and methylethylaminocarbonyl. An example of "$C_{2-6}$alkylene" is ethylene and propylene.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

The compounds of the formula (I) may be administered in the form of a pro-drug which is broken down in the human or animal body to give a compound of the formula (I). Examples of pro-drugs include in vivo hydrolysable esters and in vivo hydrolysable amides of a compound of the formula (I).

An in vivo hydrolysable ester of a compound of the formula (I) containing carboxy or hydroxy group is, for example, a pharmaceutically acceptable ester which is hydrolysed in the human or animal body to produce the parent acid or alcohol. Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of a-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

A suitable value for an in vivo hydrolysable amide of a compound of the formula (I) containing a carboxy group is, for example, a N-$C_{1-6}$alkyl or N,N-di-$C_{1-6}$alkyl amide such as N-methyl, N-ethyl, N-propyl, N,N-dimethyl, N-ethyl-N-methyl or N,N-diethyl amide.

Some compounds of the formula (I) may have chiral centres and/or geometric isomeric centres (E- and Z-isomers), and it is to be understood that the invention encompasses all such optical, diastereoisomers and geometric isomers that possess IBAT inhibitory activity.

The invention relates to any and all tautomeric forms of the compounds of the formula (I) that possess IBAT inhibitory activity.

It is also to be understood that certain compounds of the formula (I) can exist in solvated as well as unsolvated forms such as, for example, hydrated forms. It is to be understood that the invention encompasses all such solvated forms which possess IBAT inhibitory activity.

In another aspect of the present invention, there is provided a compound of formula (I):

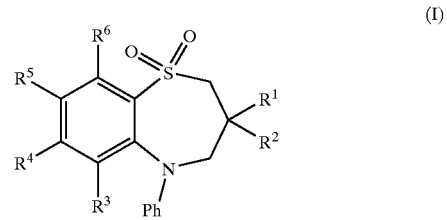

(I)

wherein:
$R^1$ and $R^2$ are independently selected from $C_{1-6}$alkyl;
one of $R^4$ and $R^5$ is a group of formula (IA):

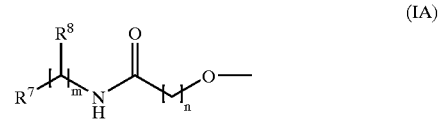

(IA)

$R^3$ and $R^6$ and the other of $R^4$ and $R^5$ are independently selected from hydrogen, halo, nitro, cyano, hydroxy, amino, carboxy, carbamoyl, mercapto, sulphamoyl, $C_{1-4}$alkyl (optionally substituted by halo), $C_{2-4}$alkenyl, $C_{2-4}$alkynyl, $C_{1-4}$alkoxy (optionally substituted by halo), $C_{1-4}$alkanoyl, $C_{1-4}$alkanoyloxy, N-($C_{1-4}$allyl)amino, N,N-($C_{1-4}$alkyl)_2$ amino, $C_{1-4}$alkanoylamino, N-($C_{1-4}$alkyl)carbamoyl, N,N-($C_{1-4}$alkyl)_2$carbamoyl, $C_{1-4}$alkylS(O)$_a$ wherein a is 0 to 2, $C_{1-4}$alkoxycarbonyl, N-($C_{1-4}$alkyl)sulphamoyl and N,N-($C_{1-4}$ alkyl)_2$sulphamoyl;

$R^7$ is carboxy, sulpho, phosphono, —P(O)(OR$^a$)(OR$^b$) or P(O)(OH)(OR$^c$) wherein R$^a$, R$^b$ and R$^c$ are independently selected from $C_{1-6}$alkyl;

$R^8$ is hydrogen or $C_{1-4}$alkyl optionally substituted by one or more hydroxy, carboxy, sulpho, amino, amidino, phosphono, $C_{1-4}$alkoxy, $C_{1-4}$alkylS(O)$_a$ wherein a is 0 to 2, —P(O)(OR$^d$)(OR$^e$) or —P(O)(OH)(OR$^f$) wherein R$^d$, R$^e$ and R$^f$ are independently selected from $C_{1-6}$alkyl;

m is 1–3;
n is 1–3;
or a pharmaceutically acceptable salt, solvate, solvate of such a salt or a prodrug thereof.

Preferred values of $R^1$, $R^2$, $R^3$, $R^4$, $R^5$, $R^6$, $R^7$, $R^8$, m and n are as follows. Such values may be used where appropriate with any of the definitions, claims or embodiments defined hereinbefore or hereinafter.

Preferably $R^1$ and $R^2$ are independently selected from $C_{1-4}$alkyl.

More preferably one of $R^1$ and $R^2$ is ethyl, propyl or butyl and the other is butyl.

Particularly one of $R^1$ and $R^2$ is ethyl and the other is butyl.

In another aspect of the invention, particularly one of $R^1$ and $R^2$ is ethyl or butyl and the other is butyl.

In a further aspect of the invention, particularly $R^1$ and $R^2$ are both butyl.

Preferably $R^3$ is hydrogen.

In one aspect of the invention, preferably $R^4$ is a group of formula (IA).

In one aspect of the invention, preferably $R^5$ is a group of formula (IA).

Preferably when $R^4$ is a group of formula (IA), $R^5$ is hydrogen, halo, hydroxy, $C_{1-4}$alkyl (optionally substituted by halo) or $C_{1-4}$alkoxy (optionally substituted by halo).

More preferably when $R^4$ is a group of formula (IA), $R^5$ is hydrogen, fluoro, chloro, bromo, hydroxy, methyl, ethyl, trifluoromethyl, methoxy, ethoxy, trifluoromethoxy or difluoromethoxy.

Particularly when $R^4$ is a group of formula (IA), $R^5$ is hydrogen, hydroxy or methoxy.

More particularly when $R^4$ is a group of formula (IA), $R^5$ is hydrogen.

Preferably when $R^5$ is a group of formula (IA), $R^4$ is hydrogen, halo, hydroxy, amino, $C_{1-4}$alkyl (optionally substituted by halo), $C_{1-4}$alkoxy (optionally substituted by halo), N-($C_{1-4}$alkyl)amino or N,N-($C_{1-4}$alkyl)$_2$amino.

More preferably when $R^5$ is a group of formula (IA), $R^4$ is hydrogen, fluoro, chloro, bromo, hydroxy, methyl, ethyl, propyl, isopropyl, butyl, trifluoromethyl, methoxy, ethoxy, propoxy, isopropoxy, butoxy, trifluoromethoxy, difluoromethoxy, amino, methylamino, ethylamino, isopropylamino, butylamino, dimethylamino or diethylamino.

Particularly when $R^5$ is a group of formula (IA), $R^4$ is hydrogen, chloro, bromo, hydroxy, methyl, ethyl, isopropyl, trifluoromethyl, methoxy, ethoxy, trifluoromethoxy, difluoromethoxy, amino, methylamino, ethylamino, dimethylamino or diethylamino.

More particularly when $R^5$ is a group of formula (IA), $R^4$ is bromo.

In another aspect of the invention, preferably when $R^5$ is a group of formula (IA), $R^4$ is halo, $C_{1-4}$alkoxy or $C_{1-4}$alkylsulphanyl.

In another aspect of the invention, preferably when $R^5$ is a group of formula (IA), $R^4$ is bromo, methoxy or methylthio.

In another aspect of the invention, preferably when $R^5$ is a group of formula (IA), $R^4$ is methylthio, ethylthio and isopropylthio.

In another aspect of the invention, preferably when $R^5$ is a group of formula (IA), $R^4$ is methylthio.

Preferably $R^6$ is hydrogen.

Preferably $R^7$ is carboxy, sulpho, phosphono or P(O)(OH)(OR$^c$) wherein $R^c$ is $C_{1-4}$alkyl.

More preferably $R^7$ is carboxy or sulpho.

In another aspect of the invention, preferably $R^7$ is carboxy, sulpho or a group of formula (IB).

In a further aspect of the invention, preferably $R^7$ is phosphono or P(O)(OH)(OR$^c$) wherein $R^c$ is $C_{1-4}$alkyl.

In one aspect of the invention, preferably $R^7$ is carboxy.

In another aspect of the invention, preferably $R^7$ is sulpho.

Preferably $R^8$ is hydrogen or $C_{1-6}$alkyl substituted by carboxy.

More preferably $R^8$ is hydrogen or $C_{1-4}$alkyl substituted by carboxy.

Particularly $R^8$ is hydrogen or 2-carboxyethyl.

More particularly $R^8$ is hydrogen.

In one aspect of the invention preferably m is 1.

In another aspect of the invention preferably m is 2.

In a further aspect of the invention preferably m is 3.

In one aspect of the invention preferably n is 1.

In another aspect of the invention preferably n is 2.

In a further aspect of the invention preferably n is 3.

Preferably for the group of formula (IA), $R^7$ is carboxy, sulpho, phosphono or P(O)(OH)(OR$^c$) wherein $R^c$ is $C_{1-4}$alkyl, $R^8$ is hydrogen or $C_{1-6}$alkyl substituted by carboxy, m is 1–3 and n is 1.

More preferably for the group of formula (IA), $R^7$ is carboxy, sulpho, phosphono or P(O)(OH)(OR$^c$) wherein $R^c$ is $C_{1-4}$alkyl, $R^8$ is hydrogen, m is 1–3 and n is 1.

Particularly for the group of formula (IA), $R^7$ is carboxy or sulpho, $R^8$ is hydrogen, m is 1–2 and n is 1.

In another aspect of the invention preferably for the group of formula (IA), $R^7$ is carboxy or sulpho, $R^8$ is hydrogen or $C_{1-6}$alkyl substituted by carboxy, m is 1–3 and n is 1.

More preferably for the group of formula (IA), $R^7$ is carboxy or sulpho, $R^8$ is hydrogen or 2-carboxyethyl, m is 1–3 and n is 1.

Particularly the group of formula (IA) is N-(carboxymethyl)carbamoylmethoxy, N-[1-(carboxyethyl)-1-(carboxy)methyl]carbamoylmethoxy, N-(2-sulphoethyl)carbamoylmethoxy or N-(3-sulphopropyl)carbamoylmethoxy.

More particularly the group of formula (IA) is N-(carboxymethyl)carbamoylmethoxy or N-(2-sulphoethyl)carbamoylmethoxy.

In one aspect of the invention, preferably the group of formula (IA) is N-(carboxymethyl)carbamoylmethoxy, N-(2-sulphoethyl)carbamoylmethoxy, N-(1,3-dicarboxypropyl)carbamoylmethoxy, N-(3-sulphopropyl)carbamoylmethoxy, N-[N-(2-sulphoethyl)carbamoylmethyl]carbamoylmethoxy, N-[1-carboxy-2-(4-hydroxyphenyl)ethyl]carbamoylmethoxy, N-(1-carboxy-2-phenylethyl)carbamoylmethoxy, N-(1-carboxy-3-methylbutyl)carbamoylmethoxy, N-(1-carboxy-2-indol-3-ylethyl)carbamoylmethoxy, N-(1-carboxy-2-pyrid-3-ylethyl)carbamoylmethoxy, N-(carboxymethyl)-N-(benzyl)carbamoylmethoxy, N-(1-carboxyethyl)carbamoylmethoxy, 1-[N-(carboxymethyl)carbamoyl]ethoxy, N-(1-carboxy-2-hydroxyethyl)carbamoylmethoxy, N-(1-carboxycycloprop-1-yl)carbamoylmethoxy, N-(1-carboxy-1-methylethyl)carbamoylmethoxy, N-(1-carboxy-2-cyclohexylethyl)carbamoylmethoxy, N-(1-carboxy-2-methylpropyl)carbamoylmethoxy, N-(1-carboxy-2-imidazol-4-ylethyl)carbamoylmethoxy, N-[1-carboxy-2-(1-methylimidazol-4-yl)ethyl]carbamoylmethoxy, N-(1-carboxy-2-t-butoxypropyl)carbamoylmethoxy, N-(1-carboxy-3-methylthiopropyl)carbamoylmethoxy, N-(1-carboxy-2-methylbutyl)carbamoylmethoxy, N-(1-carboxy-2-imethylpropyl)carbamoylmethoxy, N-(1-carboxy-1-methyl-2-indol-3-ylethyl)carbamoylmethoxy, N-(1-carboxy-2-hydroxypropyl)carbamoylmethoxy and N-(1-carboxy-1-cyclohexylmethyl)carbamoylmethoxy.

In another aspect of the invention, preferably $R^8$ and $R^9$ are independently hydrogen, $C_{1-4}$alkyl or a saturated cyclic group, or $R^8$ and $R^9$ together form $C_{2-6}$alkylene; wherein $R^8$ and $R^9$ or $R^8$ and $R^9$ together may be independently optionally substituted on carbon by one or more substituents selected from $R^{15}$; wherein $R^{15}$ is selected from hydroxy, carboxy, $C_{1-4}$alkoxy, $C_{1-4}$alkylS(O)$_a$ wherein a is 0, carbocyclyl and heterocyclyl; wherein $R^{15}$ may be optionally substituted on carbon by one or more $R^{19}$; and wherein if said heterocyclyl contains an —NH— moiety, that nitrogen may be optionally substituted by one or more $R^{23}$;

$R^{19}$ is hydroxy; and $R^{23}$ is $C_{1-4}$alkyl.

In another aspect of the invention, more preferably $R^8$ and $R^9$ are independently hydrogen, $C_{1-4}$alkyl or a cyclohexyl, or $R^8$ and $R^9$ together form $C_{2-6}$alkylene; wherein $R^8$ and $R^9$ or $R^8$ and $R^9$ together may be independently optionally substituted on carbon by one or more substituents selected from $R^{15}$; wherein $R^{15}$ is selected from hydroxy, carboxy, $C_{1-4}$alkoxy, $C_{1-4}$alkylS(O)$_a$ wherein a is 0, phenyl, pyridyl, imidazolyl and indolyl; wherein $R^{15}$ may be optionally substituted on carbon by one or more $R^{19}$; and wherein said imidazolyl and indolyl may be optionally substituted on nitrogen by one or more $R^{23}$;

$R^{19}$ is hydroxy; and $R^{23}$ is $C_{1-4}$alkyl.

In another aspect of the invention, particularly $R^8$ and $R^9$ are independently hydrogen, 2-carboxyethyl, 4-hydroxybenzyl, benzyl, iso-butyl, indol-3-ylmethyl, pyrid-3-ylmethyl, methyl, hydroxymethyl, cyclohexylmethyl, isopropyl, imidazol-4-ylmethyl, 1-methylimidazol-4-ylmethyl, 1-t-butoxyethyl, 2-methylthioethyl, sec-butyl, 1-hydroxyethyl or cyclohexyl; or $R^8$ and $R^9$ together form cyclopropyl.

In another aspect of the invention, more particularly $R^8$ is selected from hydrogen, 2-carboxyethyl, 4-hydroxybenzyl, benzyl, iso-butyl, indol-3-ylmethyl, pyrid-3-ylmethyl, methyl, hydroxymethyl, cyclohexylmethyl, isopropyl, imidazol-4-ylmethyl, 1-methylimidazol-4-ylmethyl, 1-t-butoxyethyl, 2-methylthioethyl, sec-butyl, 1-hydroxyethyl or cyclohexyl; $R^9$ is selected from hydrogen or methyl; or $R^8$ and $R^9$ together form cyclopropyl.

Preferably $R^{10}$ is hydrogen or $C_{1-4}$alkyl; wherein $R^{10}$ is optionally substituted on carbon by one or more substituents selected from $R^{24}$; wherein $R^{24}$ is carbocyclyl.

More preferably $R^{10}$ is hydrogen or benzyl.

In one aspect of the invention, particularly $R^{10}$ is hydrogen.

In another aspect of the invention, particularly $R^{10}$ is benzyl.

Preferably $R^{11}$ is hydrogen or $C_{1-4}$alkyl.

More preferably $R^{11}$ is hydrogen or methyl.

In one aspect of the invention particularly $R^{11}$ is hydrogen.

In another aspect of the invention particularly $R^{11}$ is methyl.

Preferably $R^{12}$ is hydrogen.

Preferably $R^{13}$ is carboxy or sulpho.

In one aspect of the invention, more preferably $R^{13}$ is carboxy.

In another aspect of the invention, more preferably $R^{13}$ is sulpho.

In one aspect of the invention preferably p is 1.

In another aspect of the invention preferably p is 2; wherein the values of $R^{12}$ may be the same or different.

In a further aspect of the invention preferably p is 3; wherein the values of $R^{12}$ may be the same or different.

Therefore in a further aspect of the invention, there is provided a compound of formula (I) as depicted above wherein:

$R^1$ and $R^2$ are independently selected from $C_{1-4}$alkyl;

$R^3$ is hydrogen;

$R^4$ is a group of formula (IA) and $R^5$ is hydrogen, or $R^5$ is a group of formula (IA) and $R^4$ is halo;

$R^6$ is hydrogen; and in the group of formula (IA), $R^7$ is carboxy or sulpho, $R^8$ is hydrogen or $C_{1-6}$alkyl substituted by carboxy, m is 1–3 and n is 1;

or a pharmaceutically acceptable salt, solvate, solvate of such a salt or a prodrug thereof.

Therefore in an additional aspect of the invention, there is provided a compound of formula (I) as depicted above wherein:

one of $R^1$ and $R^2$ is ethyl and the other is butyl;

$R^3$ is hydrogen;

$R^4$ is a group of formula (IA) and $R^5$ is hydrogen, or $R^5$ is a group of formula (IA) and $R^4$ is bromo;

$R^6$ is hydrogen; and the group of formula (IA) is N-(carboxymethyl)carbamoylmethoxy, N-[1-(carboxyethyl)-1-(carboxy)methyl]carbamoylmethoxy, N-(2-sulphoethyl)carbamoylmethoxy or N-(3-sulphopropyl)carbamoylmethoxy;

or a pharmaceutically acceptable salt, solvate, solvate of such a salt or a prodrug thereof.

Therefore in an additional aspect of the invention, there is provided a compound of formula (I) as depicted above wherein:

one of $R^1$ and $R^2$ is ethyl or butyl and the other is butyl;

$R^3$ is hydrogen;

$R^4$ is selected from bromo, methoxy or methylthio;

$R^5$ is a group of formula (IA);

$R^6$ is hydrogen; and the group of formula (IA) is N-(carboxymethyl)carbamoylmethoxy, N-(2-sulphoethyl)carbamoylmethoxy, N-(1,3-dicarboxypropyl)carbamoylmethoxy, N-(3-sulphopropyl)carbamoylmethoxy, N-[N-(2-sulphoethyl)carbamoylmethyl]carbamoylmethoxy, N-[1-carboxy-2-(4-hydroxyphenyl)ethyl]carbamoylmethoxy, N-(1-carboxy-2-phenylethyl)carbamoylmethoxy, N-(1-carboxy-3-methylbutyl)carbamoylmethoxy, N-(1-carboxy-2-indol-3-ylethyl)carbamoylmethoxy, N-(1-carboxy-2-pyrid-3-ylethyl)carbamoylmethoxy, N-(carboxymethyl)-N-(benzyl)carbamoylmethoxy, N-(1-carboxyethyl)carbamoylmethoxy, 1-[N-(carboxymethyl)carbamoyl]ethoxy, N-(1-carboxy-2-hydroxyethyl)carbamoylmethoxy, N-(1-carboxycycloprop-1-yl)carbamoylmethoxy, N-(1-carboxy-1-methylethyl)carbamoylmethoxy, N-(1-carboxy-2-cyclohexylethyl)carbamoylmethoxy, N-(1-carboxy-2-methylpropyl)carbamoylmethoxy, N-(1-carboxy-2-imidazol-4-ylethyl)carbamoylmethoxy, N-[1-carboxy-2-(1-methylimidazol-4-yl)ethyl]carbamoylmethoxy, N-(1-carboxy-2-t-butoxypropyl)carbamoylmethoxy, N-(1-carboxy-3-methylthiopropyl)carbamoylmethoxy, N-(1-carboxy-2-methylbutyl)carbamoylmethoxy, N-(1-carboxy-2-imethylpropyl)carbamoylmethoxy, N-(1-carboxy-1-methyl-2-indol-3-ylethyl)carbamoylmethoxy, N-(1-carboxy-2-hydroxypropyl)carbamoylmethoxy and N-(1-carboxy-1-cyclohexylmethyl)carbamoylmethoxy;

or a pharmaceutically acceptable salt, solvate, solvate of such a salt or a prodrug thereof.

In another aspect of the invention, preferred compounds of the invention are any one of Examples 1, 5, 6, 8, 9 or 10 or a pharmaceutically acceptable salt, solvate, solvate of such a salt or a prodrug thereof.

In another aspect of the invention, preferred compounds of the invention are any one of Examples or a pharmaceutically acceptable salt, solvate, solvate of such a salt or a prodrug thereof.

Preferred aspects of the invention are those which relate to the compound of formula (I) or a pharmaceutically acceptable salt thereof.

Another aspect of the present invention provides a process for preparing a compound of formula (I) or a pharmaceutically acceptable salt, solvate, solvate of such a salt or a prodrug thereof which process (wherein variable groups are, unless otherwise specified, as defined in formula (I)) comprises of:

Process 1):

Oxidising a Benzothiazepine of Formula (II):

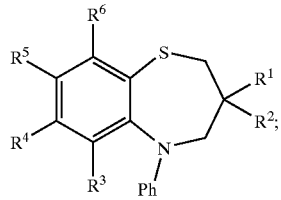
(II)

Process 2):

Reacting an Alcohol of Formula (IIIa) or (IIIb):

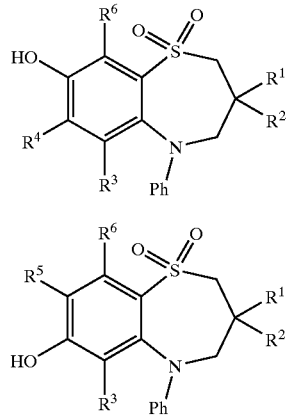
(IIIa)

(IIIb)

with a compound of formula (IV):

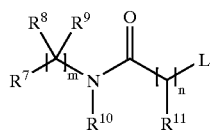
(IV)

wherein L is a displaceable group;

Process 3):
Seacting an Acid of Formula (Va) or (Vb):

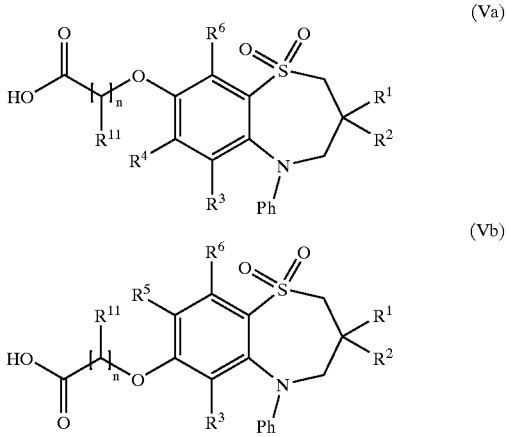
(Va)

(Vb)

or an activated derivative thereof; with an amine of formula (VI:

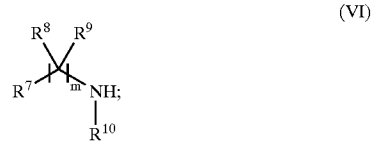
(VI)

Process 4):
for Compounds of Formula (I) wherein $R^7$ is a Group of Formula (IB); Reacting an Acid of Formula (VIIa) or (VIIb):

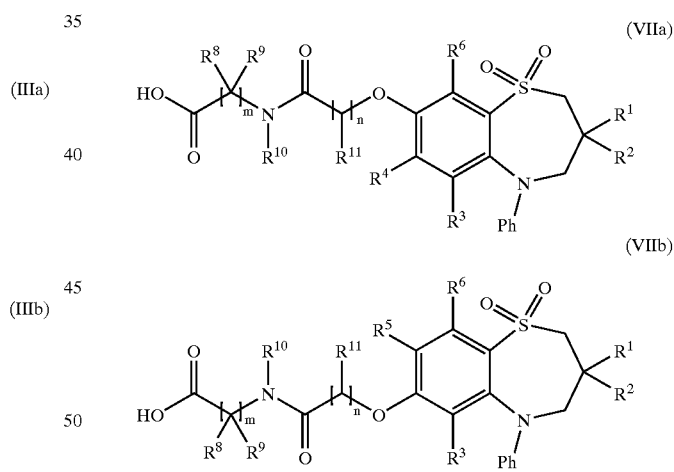
(VIIa)

(VIIb)

or an activated derivative thereof; with an amine of formula (IX):

(VI)

and thereafter if necessary or desirable:
i) converting a compound of the formula (I) into another compound of the formula (I);
ii) removing any protecting groups;
iii) forming a pharmaceutically acceptable salt, solvate, solvate of such a salt or a prodrug.

L is a displaceable group, suitable values for L are for example, a halogeno or sulphonyloxy group, for example a chloro, bromo, methanesulphonyloxy or toluene-4-sulphonyloxy group.

Specific reaction conditions for the above reactions are as follows.

1) Benzothiazepines of formula (II) may be oxidised under standard sulphur oxidation conditions; for example using hydrogen peroxide and trifluoroacetic acid at a temperature in the range of 0° C. to reflux, preferably at or near room temperature.

Compounds of formula (II) may be prepared according to the following scheme.

tetrahydrofuran at a temperature in the range of 0° C. to reflux, preferably at or near reflux.

Compounds of formula (IIIa) or (IIIb) may be prepared in a similar manner to compounds of formula (II) (but wherein $R^4$ or $R^5$ is hydroxy) followed by the oxidation step of Process 1.

Compounds of formula (IV) are commercially available compounds, or they are known in the literature, or they are prepared by standard processes known in the art.

3) Acids of formula (Va) or (Vb) and amines of formula (VI) and acids of formula (VIIa) or (VIIb) and amines of formula (IX) may be coupled together in the presence of a suitable coupling reagent. Standard peptide coupling

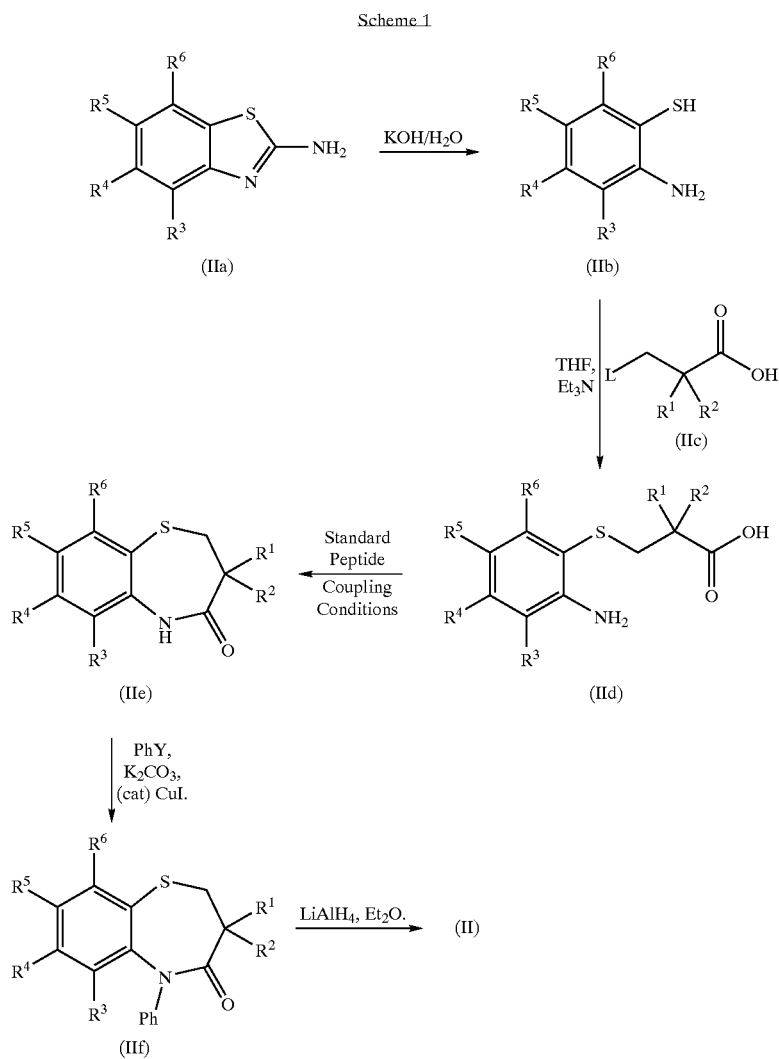

Scheme 1 wherein L is a displaceable group as defined above, and Y is a displaceable group, for example halo.

Compounds of formula (IIa) and (IIc) are commercially available compounds, or they are known in the literature, or they are prepared by standard processes known in the art.

2) Alcohols of formula (IIIa) or (IIIb) may be reacted with compounds of formula (V) in the presence of a base for example an inorganic base such as sodium carbonate, or an organic base such as Hunigs base, in the presence of a suitable solvent such as acetonitrile, dichloromethane or reagents known in the art can be employed as suitable coupling reagents, or for example carbonyldiimidazole and dicyclohexyl-carbodiimide, optionally in the presence of a catalyst such as dimethylaminopyridine or 4-pyrrolidinopyridine, optionally in the presence of a base for example triethylamine, pyridine, or 2,6-di-alkyl-pyridines such as 2,6-lutidine or 2,6-di-tert-butylpyridine. Suitable solvents include dimethylacetamide, dichloromethane, benzene, tetrahydrofuran and dimethylformamide. The coupling reaction may conveniently be performed at a temperature in the range of −40 to 40° C.

Suitable activated acid derivatives include acid halides, for example acid chlorides, and active esters, for example pentafluorophenyl esters. The reaction of these types of compounds with amines is well known in the art, for example they may be reacted in the presence of a base, such as those described above, and in a suitable solvent, such as those described above. The reaction may conveniently be performed at a temperature in the range of −40 to 40° C.

Compounds of formula (Va) or (Vb) may be prepared according to the following scheme.

Scheme 2

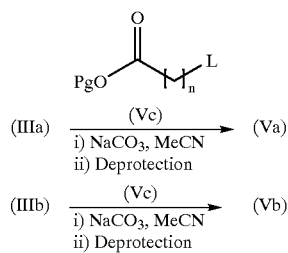

wherein L is a displaceable group as defined above and Pg is a carboxy protecting group such as those described below.

Compounds of formula (VIIa) or (VIIb) may be prepared according to the following scheme.

Scheme 3

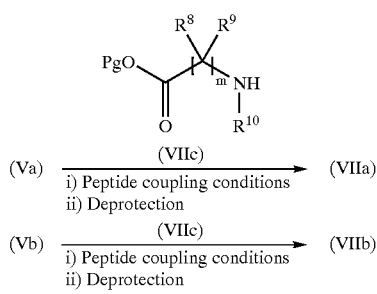

wherein Pg is an acid protecting group such as those described below.

Compounds of formula (Vc) and (VI) and compounds of formula (VIIc) and (IX) are commercially available compounds, or they are known in the literature, or they are prepared by standard processes known in the art.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide.

Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

As stated hereinbefore the compounds defined in the present invention possess IBAT inhibitory activity. These properties may be assessed, for example, using an in vitro test assay for studying the effect on bile acid uptake in IBAT-transfected cells (Smith L., Price-Jones M. J., Hugnes K. T. and Jones N. R. A.; J Biomolecular Screening, 3, 227–230) or in vivo by studying the effect on radiolabelled bile acid absorption in mice/rats (Lewis M. C., Brieaddy L. E. and Root C., J., J Lip Res 1995, 36, 1098–1105).

In the in vitro test assay described in the above reference the compound of Example 9 had an $IC_{50}$ of 2.1 µM.

According to a further aspect of the invention there is provided a pharmaceutical composition which comprises a compound of formula (I), or a pharmaceutically acceptable salt, solvate, solvate of such a salt or a prodrug thereof as defined hereinbefore in association with a pharmaceutically-acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The compound of formula (I), or a pharmaceutically acceptable salt, solvate, solvate of such a salt or a prodrug thereof, will normally be administered to a warm-blooded animal at a unit dose within the range 5–5000 mg per square meter body area of the animal, i.e. approximately 0.1–100 mg/kg, and this normally provides a therapeutically-effective dose. A unit dose form such as a tablet or capsule will usually contain, for example 1–250 mg of active ingredient. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a compound of the formula (I), or a pharmaceutically acceptable salt, solvate, solvate of such a salt or a prodrug thereof, as defined hereinbefore for use in a method of prophylactic or therapeutic treatment of a warm-blooded animal, such as man.

We have found that the compounds defined in the present invention, or a pharmaceutically acceptable salt, solvate, solvate of such a salt or a prodrug thereof, are effective IBAT inhibitors, and accordingly have value in the treatment of disease states associated with hyperlipidaemic conditions.

Thus according to this aspect of the invention there is provided a compound of the formula (I), or a pharmaceutically acceptable salt, solvate, solvate of such a salt or a prodrug thereof, as defined hereinbefore for use as a medicament.

According to another feature of the invention there is provided the use of a compound of the formula (I), or a pharmaceutically acceptable salt, solvate, solvate of such a salt or a prodrug thereof, as defined hereinbefore in the manufacture of a medicament for use in the production of an IBAT inhibitory effect in a warm-blooded animal, such as man.

According to another feature of the invention there is provided the use of a compound of the formula (I), or a pharmaceutically acceptable salt, solvate, solvate of such a salt or a prodrug thereof, as defined hereinbefore in the manufacture of a medicament for use in the treatment of hyperlipidaemic conditions in a warm-blooded animal, such as man.

According to a further feature of this aspect of the invention there is provided a method for producing an IBAT inhibitory effect in a warm-blooded animal, such as man, in need of such treatment which comprises administering to said animal an effective amount of a compound of formula (I), or a pharmaceutically acceptable salt, solvate, solvate of such a salt or a prodrug thereof.

The size of the dose required for the therapeutic or prophylactic treatment will necessarily be varied depending on the host treated, the route of administration and the severity of the illness being treated. A unit dose in the range, for example, 1–100 mg/kg, preferably 1–50 mg/kg is envisaged.

The IBAT inhibitory activity defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. According to this aspect of the invention there is provided a pharmaceutical product comprising a compound of the formula (I), or a pharmaceutically acceptable salt, solvate, solvate of such a salt or a prodrug thereof, as defined hereinbefore and an additional IBAT inhibitory substance as defined hereinbefore and an additional hypolipidaemic agent for the conjoint treatment of hyperlipidaemia.

In another aspect of the invention, the compound of formula (I), or a pharmaceutically acceptable salt, solvate, solvate of such a salt or a prodrug thereof, may be administered in association with an HMG Co-A reductase inhibitor, or pharmaceutically acceptable salts, solvates, solvates of such salts or prodrugs thereof. Suitable HMG Co-A reductase inhibitors, pharmaceutically acceptable salts, solvates, solvates of such salts or prodrugs thereof are statins well known in the art. Particular statins are fluvastatin, lovastatin, pravastatin, simvastatin, atorvastatin, cerivastatin, bervastatin, dalvastatin, mevastatin and (E)-7-[4-(4-fluorophenyl)-6-isopropyl-2-[methyl (methylsulphonyl)amino]pyrimidin-5-yl](3R,5S)-3,5-dihydroxyhept-6-enoic acid, or a pharmaceutically acceptable salt, solvate, solvate of such a salt or a prodrug thereof A particular statin is atorvastatm, or a pharmaceutically acceptable salt, solvate, solvate of such a salt or a prodrug thereof. A further particular statin is (E)-7-[4-(4-fluorophenyl)-6-isopropyl-2-[methyl(methylsulphonyl) amino]pyrimidin-5-yl](3R,5S)-3,5-dihydroxyhept-6-enoic acid, or a pharmaceutically acceptable salt, solvate, solvate of such a salt or a prodrug thereof.

In an additional aspect of the invention, the compound of formula (1), or a pharmaceutically acceptable salt, solvate, solvate of such a salt or a prodrug thereof may be administered in association with an HMG Co-A reductase inhibitor, or a pharmaceutically acceptable salt, solvate, solvate of such a salt or a prodrug thereof, and/or a bile acid binder thereby avoiding a possible risk of excess of bile acids in colon caused by the inhibition of the ileal bile acid transport system. An excess of bile acids in the visceral contents may cause diarrhoea. Thus, the present invention also provides a treatment of a possible side effect such as diarrhoea in patients during therapy comprising the compound of formula (I), or a pharmaceutically acceptable salt, solvate, solvate of such a salt or a prodrug thereof.

An HMG CoA-reductase inhibitor, or a pharmaceutically acceptable salt, solvate, solvate of such a salt or a prodrug thereof will by its action decrease the endogenous cholesterol available for the bile acid synthesis and have an additive effect in combination with the compound of formula (I), or a pharmaceutically acceptable salt, solvate, solvate of such a salt or a prodrug thereof on lipid lowering.

Suitable bile acid binders for such a combination therapy are resins, such as cholestyramine and cholestipol. One advantage is that the dose of bile acid binder might be kept lower than the therapeutic dose for treatment of cholesterolaemia in single treatment comprising solely a bile acid binder. By a low dose of bile acid binder any possible side effects caused by poor tolerance of the patient to the therapeutic dose could also be avoided.

Therefore in an additional feature of the invention, there is provided a method for producing an IBAT inhibitory effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of an HMG Co-A reductase inhibitor, or a pharmaceutically acceptable salt, solvate, solvate of such a salt or a prodrug thereof.

Therefore in an additional feature of the invention, there is provided a method for producing an IBAT inhibitory effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with a bile acid binder.

Therefore in an additional feature of the invention, there is provided a method for producing an IBAT inhibitory effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of an HMG Co-A reductase inhibitor, or a pharmaceutically acceptable salt, solvate, solvate of such a salt or a prodrug thereof, in simultaneous, sequential or separate administration with a bile acid binder.

Therefore in an additional feature of the invention, there is provided a method of treating hyperlipidemic conditions in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of an HMG Co-A reductase inhibitor, or a pharmaceutically acceptable salt, solvate, solvate of such a salt or a prodrug thereof.

Therefore in an additional feature of the invention, there is provided a method of treating hyperlipidemic conditions in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a bile acid binder.

Therefore in an additional feature of the invention, there is provided a method of treating hyperlipidemic conditions in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of an HMG Co-A reductase inhibitor, or a pharmaceutically acceptable salt, solvate, solvate of such a salt or a prodrug thereof, in simultaneous, sequential or separate administration with a bile acid binder.

According to a further aspect of the invention there is provided a pharmaceutical composition which comprises a compound of formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof, in association with a pharmaceutically acceptable diluent or carrier.

According to a further aspect of the invention there is provided a pharmaceutical composition which comprises a compound of formula (I), or a pharmaceutically acceptable salt, solvate, solvate of such a salt or a prodrug thereof, and a bile acid binder, in association with a pharmaceutically acceptable diluent or carrier.

According to a further aspect of the invention there is provided a pharmaceutical composition which comprises a compound of formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof, and a bile acid binder in association with a pharmaceutically acceptable diluent or carrier.

According to a further aspect of the present invention there is provided a kit comprising a compound of formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof.

According to a further aspect of the present invention there is provided a kit comprising a compound of formula (I), or a pharmaceutically acceptable salt, solvate, solvate of such a salt or a prodrug thereof, and a bile acid binder.

According to a further aspect of the present invention there is provided a kit comprising a compound of formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof and a bile acid binder.

According to a further aspect of the present invention there is provided a kit comprising:
a) a compound of formula (I), or a pharmaceutically acceptable salt, solvate, solvate of such a salt or a prodrug thereof, in a first unit dosage form;
b) an HMG Co-A reductase inhibitor, or a pharmaceutically acceptable salt, solvate, solvate of such a salt or a prodrug thereof; in a second unit dosage form; and
c) container means for containing said first and second dosage forms.

According to a further aspect of the present invention there is provided a kit comprising:
a) a compound of formula (I), or a pharmaceutically acceptable salt, solvate, solvate of such a salt or a prodrug thereof, in a first unit dosage form;
b) a bile acid binder; in a second unit dosage form; and
c) container means for containing said first and second dosage forms.

According to a further aspect of the present invention there is provided a kit comprising:
a) a compound of formula (I), or a pharmaceutically acceptable salt, solvate, solvate of such a salt or a prodrug thereof in a first unit dosage form;
b) an HMG Co-A reductase inhibitor, or a pharmaceutically acceptable salt, solvate, solvate of such a salt or a prodrug thereof; in a second unit dosage form;
c) a bile acid binder; in a third unit dosage form; and
d) container means for containing said first, second and third dosage forms.

According to a further aspect of the present invention there is provided a kit comprising:
a) a compound of formula (I), or a pharmaceutically acceptable salt, solvate, solvate of such a salt or a prodrug thereof, together with a pharmaceutically acceptable diluent or carrier, in a first unit dosage form;
b) an HMG Co-A reductase inhibitor, or a pharmaceutically acceptable salt, solvate, solvate of such a salt or a prodrug thereof, in a second unit dosage form; and c) container means for containing said first and second dosage forms.

According to a further aspect of the present invention there is provided a kit comprising:
a) a compound of formula (I), or a pharmaceutically acceptable salt, solvate, solvate of such a salt or a prodrug thereof, together with a pharmaceutically acceptable diluent or carrier, in a first unit dosage form;
b) a bile acid binder, in a second unit dosage form; and
c) container means for containing said first and second dosage forms.

According to a further aspect of the present invention there is provided a kit comprising:
a) a compound of formula (I), or a pharmaceutically acceptable salt, solvate, solvate of such a salt or a prodrug thereof, together with a pharmaceutically acceptable diluent or carrier, in a first unit dosage form;
b) an HMG Co-A reductase inhibitor, or a pharmaceutically acceptable salt, solvate, solvate of such a salt or a prodrug thereof, in a second unit dosage form; and
c) a bile acid binder; in a third unit dosage form; and
d) container means for containing said first, second and third dosage forms.

According to another feature of the invention there is provided the use of a compound of the formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof, in the manufacture of a medicament for use in the production of an IBAT inhibitory effect in a warm-blooded animal, such as man.

According to another feature of the invention there is provided the use of a compound of the formula (I), or a pharmaceutically acceptable salt, solvate, solvate of such a salt or a prodrug thereof, and a bile acid binder, in the manufacture of a medicament for use in the production of an IBAT inhibitory effect in a warm-blooded animal, such as man.

According to another feature of the invention there is provided the use of a compound of the formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof, and a bile acid binder, in the manufacture of a medicament for use in the production of an IBAT inhibitory effect in a warm-blooded animal, such as man.

According to another feature of the invention there is provided the use of a compound of the formula (I), or a pharmaceutically acceptable salt, solvate, solvate of such a salt or a prodrug thereof, an HMG Co-A reductase inhibitor, or a pharmaceutically acceptable salt, solvate, solvate of such a salt or a prodrug thereof, in the manufacture of a medicament for use in the treatment of hyperlipidaemic conditions in a warm-blooded animal, such as man.

According to another feature of the invention there is provided the use of a compound of the formula (I), or a pharmaceutically acceptable salt, solvate, solvate of such a salt or a prodrug thereof, a bile acid binder, in the manufacture of a medicament for use in the treatment of hyperlipidaemic conditions in a warm-blooded animal, such as man.

According to another feature of the invention there is provided the use of a compound of the formula (I), or a pharmaceutically acceptable salt, solvate, solvate of such a salt or a prodrug thereof, an HMG Co-A reductase inhibitor, or a pharmaceutically acceptable salt, solvate, solvate of such a salt or a prodrug thereof, and a bile acid binder, in the manufacture of a medicament for use in the treatment of hyperlipidaemic conditions in a warm-blooded animal, such as man.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of an HMG Co-A reductase inhibitor, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

According to a further aspect of the present invention there is provided a combination) treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of a bile acid binder, optionally together with a pharmaceutically acceptable diluent or carrier to a warm-blooded animal, such as man in need of such therapeutic treatment.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of an HMG Co-A reductase inhibitor, or a pharmaceutically acceptable salt, solvate, solvate of such a salt or a prodrug thereof, optionally together with a pharmaceutically acceptable excipient, with the simultaneous, sequential or separate administration of an effective amount of a bile acid binder, optionally together with a pharmaceutically acceptable diluent or carrier to a warm-blooded animal, such as man in need of such therapeutic treatment.

In addition to their use in therapeutic medicine, the compounds of formula a), or a pharmaceutically acceptable salt, solvate, solvate of such a salt or a prodrug thereof, are also useful as pharmacological tools in the development and standardisation of in vitro and in vivo test systems for the evaluation of the effects of inhibitors of IBAT in laboratory animals such as cats, dogs, rabbits, monkeys, rats and mice, as part of the search for new therapeutic agents.

Many of the intermediates described herein are novel and are thus provided as a further feature of the invention. For example compounds of formula (Va) and (Vb) and/or compounds of formula (VIIa) and (VIIb) show IBAT inhibitory activity when tested in the above referenced in vitro test assay and are thus claimed as a further feature of the invention.

Thus in a further feature of the invention, there is provided a compound of formula (Va) or (Vb) and/or a compound of formula (VIIa) or (VIIb), or a pharmaceutically acceptable salt, solvate, solvate of such a salt or a prodrug thereof.

Therefore according to a further aspect of the invention there is provided a pharmaceutical composition which comprises a compound of formula (Va) or (Vb) and/or a compound of formula (VIIa) or (VIIb), or a pharmaceutically acceptable salt, solvate, solvate of such a salt or a prodrug thereof, as defined hereinbefore in association with a pharmaceutically-acceptable diluent or carrier.

According to an additional aspect of the present invention there is provided a compound of the formula (Va) or (Vb) and/or a compound of formula (VIIa) or (VIIb), or a pharmaceutically acceptable salt, solvate, solvate of such a salt or a prodrug thereof, as defined hereinbefore for use in a method of prophylactic or therapeutic treatment of a warm-blooded animal, such as man.

Thus according to this aspect of the invention there is provided a compound of the formula (Va) or (Vb) and/or a compound of formula (VIIa) or (VIIb), or a pharmaceutically acceptable salt, solvate, solvate of such a salt or a prodrug thereof, as defined hereinbefore for use as a medicament.

According to another feature of the invention there is provided the use of a compound of the formula (Va) or (Vb) and/or a compound of formula (VIIa) or (VIIb), or a pharmaceutically acceptable salt, solvate, solvate of such a salt or a prodrug thereof as defined hereinbefore in the manufacture of a medicament for use in the production of an IBAT inhibitory effect in a warm-blooded animal, such as man.

According to another feature of the invention there is provided the use of a compound of the formula (Va) or (Vb) and/or a compound of formula (VIIa) or (VIIb), or a pharmaceutically acceptable salt, solvate, solvate of such a salt or a prodrug thereof as defined hereinbefore in the manufacture of a medicament for use in the treatment of hyperlipidaemic conditions in a warm-blooded animal, such as man.

According to a further feature of this aspect of the invention there is provided a method for producing an IBAT inhibitory effect in a warm-blooded animal, such as man, in need of such treatment which comprises administering to said animal an effective amount of a compound of formula (Va) or (Vb) and/or a compound of formula (VIIa) or (VIIb), or a pharmaceutically acceptable salt, solvate, solvate of such a salt or a prodrug thereof.

In the above other pharmaceutical composition, process, method, use and medicament manufacture features, the alternative and preferred embodiments of the compounds of the invention described herein also apply.

EXAMPLES

The invention will now be illustrated in the following non limiting Examples, in which standard techniques known to the skilled chemist and techniques analogous to those described in these Examples may be used where appropriate, and in which, unless otherwise stated:
(i) evaporations were carried out by rotary evaporation in vacuo and work up procedures were carried out after removal of residual solids such as drying agents by filtration;
(ii) all reactions were carried out under an inert atmosphere at ambient temperature, typically in the range 18–25° C., with solvents of HPLC grade under anhydrous conditions, unless otherwise stated;
(iii) column chromatography (by the flash procedure) was performed on Silica gel 40–63 $\mu$m (Merck);
(iv) yields are given for illustration only and are not necessarily the maximum attainable;
(v) the structures of the end products of the formula (I) were generally confirmed by nuclear (generally proton) magnetic resonance (NMR) and mass spectral techniques; magnetic resonance chemical shift values were measured in deuterated $CDCl_3$ (unless otherwise stated) on the delta scale (ppm downfield from tetramethylsilane); proton data is quoted unless otherwise stated; spectra were recorded on a Varian Mercury-300 MHz, Varian Unity plus-400 MHz, Varian Unity plus-600 MHz or on Varian Inova-500 MHz spectrometer; and peak multiplicities are shown as follows: s, singlet; d, doublet; dd, double doublet; t, triplet; tt, triple triplet; q, quartet; tq, triple quartet; m, multiplet; br, broad;

LCMS were recorded on a Waters ZMD, LC column xTerra MS $C_8$(Waters), detection with a HP 1100 MS-detector diode array equipped; mass spectra (MS) (loop) were recorded on VG Platform II (Fisons Instruments) with a HP-1100 MS-detector diode array equipped;

(vi) unless further details are specified in the text, analytical high performance liquid chromatography (HPLC) was performed on Prep LC 2000 (Waters), Cromasil $C_8$, 7 $\mu$m, (Akzo Nobel); acetonitrile and de-ionised water 100 mM ammonium acetate as mobile phases, with suitable composition;

(vii) TLC was performed on Silica gel 60 $F_{254}$ (Merck) with detection by UV light and charring with PAA (para-anisaldehyde, ethanol and sulphuric acid) if necessary.

(ix) intermediates were not generally filly characterised and purity was assessed by thin layer chromatography (TLC), HPLC, infra-red (IR), MS or NMR analysis;

(x) where solutions were dried sodium sulphate was the drying agent;

(xi) the following abbreviations may be used hereinbefore or hereinafter:

| | |
|---|---|
| DCM | dichloromethane; |
| DMF | N,N-dimethylformamide; |
| MeCN | acetonitrile; |
| AcOH | acetic acid; |
| TFA | trifluoroacetic acid; |
| TBTU | o-Benzotriazol-1-yl-N,N,N'N'-tetramethyluronium tetrafluoroborate; |
| DIPEA | di-isopropylethylamine; and |
| THF | tetrahydrofuran; |

(xii) where an "ISOLUTE" column is referred to, this means a column containing 2 g of silica, the silica being contained in a 6 ml disposable syringe and supported by a porous disc of 54 Å pore size, obtained from International Sorbent Technology under the name "ISOLUTE"; "ISOLUTE" is a registered trade mark;

EXAMPLE 1

1,1-Dioxo-3-butyl-3-ethyl-5-phenyl-7-[N-(carboxymethyl)carbamoylmethoxy]-2,3,4,5-tetrahydro-1,5-benzothiazepine 1,1-Dioxo-3-butyl-3-ethyl-5-phenyl-7-[N-(t-butoxycarbonylmethyl)carbamoylmethoxy]-2,3,4,5-tetrahydro-1,5-benzothiazepine (Method 5; 70 mg, 0.13 mmol) was dissolved in DCM (3 ml). TFA (0.5 ml) was added and the mixture was stirred at room temperature for 2 h. The reaction mixture was evaporated under reduced pressure. The residue was placed on a silica column and the product was eluted with DCM/methanol (85:15). 54 mg (86%) of the title compound was obtained. NMR (500 MHz): 0.7–0.9 (m, 6H), 1.1–1.7 (m, 8H), 3.1–3.3 (m, 2H), 3.6–3.8 (br d, 2H), 4.2 (d, 2H), 4.6 (s, 2H), 6.9–7.3 (m, 8H), 7.6 (d, 1H).

EXAMPLES 2–4

The following compounds were synthesised from the appropriate starting materials by the procedure of Example 1.

| Ex | R¹ | R² | NMR | m/z | SM |
|---|---|---|---|---|---|
| 2 | HO-C6H4-CH2-CH(COOH)-NH-C(=O)-CH2-O- (tyrosine derivative, ethyl ester on O) | Et | (400 Mhz) 0.6–0.8 (m, 6H), 0.9–1.6 (m, 8H), 2.9 (brs, 2H), 3.1–3.3 (m, 2H), 3.7 (brs, 2H), 4.3–4.6 (m, 3H), 6.6 (m, 2H), 6.9–7.1 (m, 6H), 7.2–7.4 (m, 4H) | 674.3 | Meth 11 |
| 3 | HO-C6H4-CH2-CH(COOH)-NH-C(=O)-CH2-O- (tyrosine derivative) | n-Bu | (500 MHz) 0.7–0.8 (m, 6H), 0.9–1.6 (m, 12H), 3.0 (brs, 2H), 3.2 (brs, 2H), 3.6–3.8 (m, 2H), 4.4 (m, 2H), 4.6 (s, 1H), 6.6 (d, 2H), 6.9–7.1 (m, 6H), 7.2–7.4 (m, 4H) | 701.7 | Meth 12 |
| 4 | HO-CH2-CH(COOH)-NH-C(=O)-CH2-O- (serine derivative) | n-Bu | (500 MHz) 0.7–0.8 (m, 6H), 0.9–1.6 (m, 12H), 3.2 (brs, 2H), 3.5–3.9 (m, 4H), 4.4 (brs, 1H), 4.6 (m, 2H), 6.9–7.1 (m, 4H), 7.2–7.3 (m, 2H), 7.4 (s, 1H), 7.9 (d, 1H) | 625.6 | Meth 13 |

EXAMPLE 5
1,1-Dioxo-3-butyl-3-ethyl-5-phenyl-7-bromo-8-[N-(carboxymethyl)carbamoylmethoxy]-2,3,4,5-tetrahydro-1,5-benzothiazepine The title compound was synthesised from 1,1-dioxo-3-butyl-3-ethyl-5-phenyl-7-bromo-8-[N-(t-butoxycarbonylmethyl)carbamoylmethoxy]-2,3,4,5-tetrahydro-1,5-benzothiazepine (Method 6) by the procedure of Example 1. NMR (300 MHz): 0.7–0.8 (m, 6H), 0.9–1.6 (m, 8H), 3.1–3.3 (m, 2H), 3.7 (brs, 2H), 3.9 (brs, 2H), 4.6 (s, 2H), 6.9–7.1 (m, 4H), 7.2 (m, 2H), 7.5 (s, 1H), 7.7 (brs, 1H).

EXAMPLE 6
1,1-Dioxo-3-butyl-3-ethyl-5-phenyl-7-bromo-8-[N-S-(1,3-dicarboxypropyl)carbamoylmethoxy]-2,3,4,5-tetrahydro-1,5-benzothiazepine To 1,1-dioxo-3-butyl-3-ethyl-5-phenyl-7-bromo-8-[N-S-(1,3-diethoxycarbonylpropyl)carbamoylmethoxy]-2,3,4,5-tetrahydro-1,5-benzothiazepine (Method 7; 127 mg, 0.18 mmol) was added THF (2 ml), water (1 ml) and LiOH (15 mg, 0.63 mmol). The reaction mixture was stirred at room temperature for 3 h and then was the solvent removed under reduced pressure. The crude product was then dissolved in MeCN/water (9:1), purified by HPLC to give a yield of the product of 85 mg (73%/0) as a white solid. MS: 638.2 (M+H)$^+$.

EXAMPLES 7

The following compound was synthesised from the appropriate starting materials by the procedure of Example 6.

| Ex | R¹ | NMR | SM |
|---|---|---|---|
| 7 | ![structure] | (400 MHz): 0.7–0.75 (m, 6H), 1.0–1.5 (m, 8H), 1.55 (d, 3H), 2.0 (s, 3H), 3.1–3.25 (m, 2H), 3.6–3.95 (m, 4H), 4.8 (q, 1H), 6.95–7.35 (m, 7H), 7.5 (s, 1H), 7.7 (s, 1H) | Meth 9 |

EXAMPLE 8

1,1-Dioxo-3-butyl-3-ethyl-5-phenyl-7-bromo-8-[N-(2-sulphoethyl)carbamoylmethoxy]-2,3,4,5-tetrahydro-1,5-benzothiazepine 1,1-Dioxo-3-butyl-3-ethyl-5-phenyl-7-bromo-8-(carboxymethoxy)-2,3,4,5-tetrahydro-1,5-benzothiazepine (Method 2; 70 mg, 0.137 mmol, taurine (20 mg, 0.160 mmol) and DIPEA (100 mg, 0.78 mmol) were added to DMF (2 ml). The mixture was stirred for 15 min at 50° C. TBTU (60 mg, 0.187 mmol) was added and the mixture was stirred for 1 h at 50° C. The solvent was evaporated under reduced pressure. The residue was purified by preparative HPLC using MeCN/ammonium acetate buffer (45:55) as eluent. 35 mg (40%) of the title compound (as ammonium salt) was obtained. NMR (500 MHz): 0.6–0.8 (m, 6H), 0.9–1.6 (m, 8H), 3.1–3.3 (m, 4H), 3.6–3.8 (brs, 4H), 4.6 (s, 2H), 6.9–7.1 (m, 4H), 7.2 (m, 2H), 7.4 (s, 1H), 7.7 (brs, 1H).

EXAMPLES 9–11

The following compounds were synthesised by the procedure of Example 8.

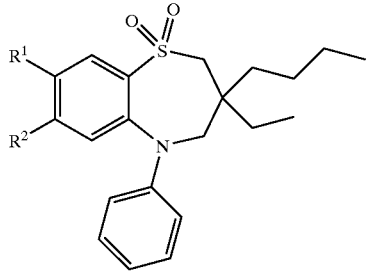

| Ex | R¹ | R² | NMR | SM |
|---|---|---|---|---|
| 9 | HOS(O)₂(CH₂)₃NH—C(O)CH₂O— | Br | 500 Mhz: 0.6–0.8 (m, 6H), 0.9–1.6 (m, 8H), 2.0 (brs, 2H), 2.9 (brs, 2H), 3.2 (m, 2H), 3.4 (brs, 2H), 3.7 (brs, 2H), 4.6 (s, 2H), 6.9–7.1 (m, 4H), 7.2 (m, 2H), 7.4 (brs, 1H), 7.5 (s, 1H) | Meth 2 |
| 10 | H | HOS(O)₂(CH₂)₂NH—C(O)CH₂O— | 300 MHz: 0.6–0.8 (m, 6H), 0.9–1.6 (m, 8H), 3.1 (brs, 4H), 3.6 (brs, 4H), 4.4 (s, 2H), 6.8–7.2 (m, 7H), 7.4 (brs, 1H), 7.5 (s, 1H) | Meth 1 |
| 11 | HOS(O)₂(CH₂)₂NH—C(O)CH₂NHC(O)—CH₂O— | Br | 0.6–0.8 (m, 6H), 0.9–1.6 (m, 8H), 3.0–3.2 (m, 4H), 3.6 (brs, 4H), 4.0 (s, 2H), 4.6 (s, 2H), 6.9–7.1 (m, 4H), 7.2 (m, 2H), 7.5 (s, 1H), 7.8 (brs, 2H) | Ex 5 |

EXAMPLE 12

1,1-Dioxo-3-butyl-3-ethyl-5-phenyl-7-bromo-8-{N-R-[1-carboxy-2-(pyrid-3-yl)ethyl]carbamoylmethoxy}-2,3,4,5-tetrahydro-1,5-benzothiazepine 1,1-Dioxo-3-butyl-3-ethyl-5-phenyl-7-bromo-8-{N-R-[1-methoxycarbonyl-2-(pyrid-3-yl)ethyl]carbamoylmethoxy}-2,3,4,5-tetrahydro-1,5-benzothiazepine (Method 8; 85 mg, 0.13 mmol) was dissolved in ethanol (2 ml). NaOH (40 mg in 0.1 nil water) was added to the solution and the mixture was stirred at 50° C. for 15 min. AcOH (0.1 ml) was added. The reaction mixture was evaporated under reduced pressure. The residue was purified by preparative HPLC using MeCN/ammonium acetate buffer (40:60) as eluent to yielded 56 mg (67%) of the title compound. NMR (500 MHz) 0.7–0.8 (m, 6H), 0.9–1.6 (m, 8H), 3.1–3.3 (m, 4H), 3.6–3.8 (m, 2H), 4.6 (s, 2H), 4.8 (s, 1H), 7.0–7.1 (m, 4H), 7.3–7.4 (m, 3H), 7.45 (s, 1H), 7.6 (m, 1H), 7.7 (m, 1H), 8.4 (s, 1H), 8.5 (s, 1H).

EXAMPLE 13

The following compound was synthesised from the appropriate starting materials by the procedure of Example 12.

| Ex | R$^1$ | NMR | SM |
|---|---|---|---|
| 13 | [structure] | (400 MHz) 0.6–0.8 (m, 6H), 0.9–1.6 (m, 8H), 2.9 (brs, 2H), 3.1–3.3 (m, 2H), 3.7 (brs, 2H), 3.9 (brs, 1H), 4.0 (brs, 1H), 4.6–4.7 (m, 2H), 5.0 (s, 2H), 7.0–7.5 (m, 12H) | Meth 10 |

EXAMPLES 14

1,1-Dioxo-3-butyl-3-ethyl-5-phenyl-7-bromo-8-{N-S-[1-carboxy-3-methylbutyl]carbamoylmethoxy}-2,3,4,5-tetrahydro-1,5-benzothiazepine 1,1-Dioxo-3-butyl-3-ethyl-5-phenyl-7-bromo-8-{N-S-[1-methoxycarbonyl-3-methylbutyl]carbamoylmethoxy}-2,3,4,5-tetrahydro-1,5-benzothiazepine (Method 15; 53 mg, 0.083 mmol) was dissolved in THF (1 ml). Water (1 ml) and LiOH (monohydrate) (11 mg, 0.26 mg) were added. The reaction mixture was stirred at room temperature for 3.5 hours. Water was added and the solution was acidified with HCl-solution (aq, 2M). The water-layer was extracted twice with EtOAc. The combined organic layer was washed once with brine, dried, filtered and evaporated under reduced pressure. The residue was purified by preparative HPLC using an MeCN/ammonium acetate buffer gradient (5/95 to 100/0) as eluent to yield 44 mg (85%) of the title compound. NMR (400 MHz, CD$_3$OD) 0.73–0.86 (m, 6H), 0.94 (d, 6H), 0.99–1.3 (m, 4H), 1.3–1.76 (m, 7H), 3.27 (brs, 2H), 3.6–3.9 (m, 2H), 4.47–4.53 (m, 1H) (ABq, 2H), 7.02 (brt, 1H), 7.09–7.16 (m, 3H), 7.31 (brt, 2H), 7.52 (s, 1H).

EXAMPLES 15–35

The following compounds were synthesised from the appropriate starting materials by the procedure of Example 14.

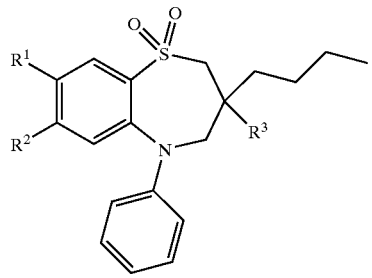

| Ex | R¹ | R² | R³ | NMR | SM |
|---|---|---|---|---|---|
| 15[1] | (phenylalanine-CH₂OCH(CH₃)- derivative with HOOC-CH(CH₂Ph)-NH-C(O)-CH₂-O-) | Br | Et | (400 MHz) 0.73–0.85 (m, 6H), 0.98–1.28 (m, 4H), 1.3–1.54 (m, 3H), 1.54–1.71 (m, 1H), 3.13–3.34 (m, 4H), 3.60–3.86 (m, 2H), 4.57 (ABq, 2H), 5.01 (q, 1H), 7.04–7.13 (m, 4H), 7.16–7.37 (m, 8H), 7.46 (s, 1H) | Meth 14 |
| 16 | (tryptophan derivative with HOOC-CH(CH₂-indolyl)-NH-C(O)-CH₂-O-) | Br | Et | (400 MHz, CD₃OD) 0.73–0.87 (m, 6H), 0.99–1.3 (m, 4H), 1.3–1.66 (m, 4H), 3.25 (brs, 2H), 3.29–3.44 (m, 2H), 3.52–3.92 (m, 2H), 4.59 (ABq, 2H), 4.79–4.90 (m, 1H), 6.92 (t, 1H), 7.0–7.07 (m, 3H), 7.07–7.16 (m, 3H), 7.26–7.35 (m, 3H), 7.45 (s, 1H), 7.51 (d, 1H), 7.72 (brd, NH), 10.29 (brs, NH) | Meth 16 |
| 17[2] | (phenylalanine derivative with HOOC-CH(CH₂Ph)-NH-C(O)-CH₂-O-) | MeO | Et | (400 MHz) 0.73–0.88 (m, 6H), 1.0–1.3 (m, 4H), 1.3–1.56 (m, 3H), 1.56–1.75 (m, 1H), 3.09–3.31 (m, 4H), 3.49 (s, 3H), 3.6–3.9 (m, 2H), 4.55 (s, 2H), 4.97 (q, 1H), 6.34 (s, 1H), 7.03 (t, 1H), 7.07–7.35 (m, 9H), 7.47 (brd, NH), 7.53 (s, 1H) | Meth 19 |
| 18[3] | (tryptophan derivative with HOOC-CH(CH₂-indolyl)-NH-C(O)-CH₂-O-) | Br | Et | (400 MHz, CD₃OD) 0.73–0.83 (m, 6H), 0.98–1.26 (m, 4H), 1.35–1.65 (m, 4H), 3.25 (brs, 2H), 3.30–3.44 (m, 2H), 3.5–3.9 (m, 2H), 4.59 (Abq, 2H), 4.81–4.89 (m, 1H), 6.92 (t, 1H), 6.99–7.06 (m, 3H), 7.07–7.14 (m, 3H), 7.26–7.34 (m, 3H), 7.45 (s, 1H), 7.51 (d, 1H) | Meth 21 |
| 19[4] | (alanine derivative HOOC-CH(CH₃)-NH-C(O)-CH₂-O-) | Br | Et | (400 Mhz, CD₃OD) 0.73–0.88 (m, 6H), 0.98–1.3 (m, 4H), 1.35–1.65 (m, 7H), 3.28 (brs, 2H), 3.6–3.9 (m, 2H), 4.47–4.56 (m, 1H), 4.68 (s, 2H), 7.03 (t, 1H), 7.09–7.2 (m, 3H), 7.31 (t, 2H), 7.53 (s, 1H), 8.14 (brd, NH) | Meth 22 |
| 20 | (alanine derivative HOOC-CH(CH₃)-NH-C(O)-CH₂-O-) | Br | Et | (400 MHz, CD₃OD) 0.73–0.85 (m, 6H), 0.99–1.27 (m, 4H), 1.37–1.65 (m, 7H), 3.28 (brs, 2H), 3.6–3.9 (m, 2H), 4.47–4.56 (m, 1H), 4.68 (s, 2H), 7.03 (t, 1H), 7.08–7.19 (m, 3H), 7.30 (brt, 2H), 7.52 (s, 1H), 8.14 (brd, NH) | Meth 23 |

-continued

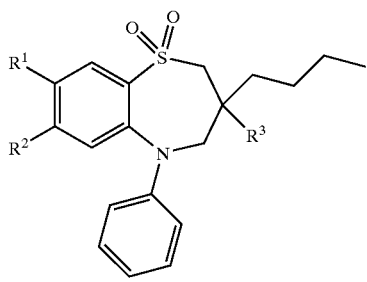

| Ex | R¹ | R² | R³ | NMR | SM |
|---|---|---|---|---|---|
| 21[5] | (cyclopropane with HOOC- and -NHC(O)CH₂O-Et group) | Br | Et | (400 Mhz, CD₃OD) 0.74–0.83 (m, 6H), 1.0–1.25 (m, 6H), 1.36–1.64 (m, 6H), 3.27 (brs, 2H), 3.6–3.9 (m, 2H), 4.65 (s, 2H), 7.03 (t, 1H), 7.08–7.16 (m, 3H), 7.31 (t, 2H), 7.47 (s, 1H) | Meth 24 |
| 22[5] | (α,α-dimethyl amino acid with -NHC(O)CH₂O-Et) | Br | Et | (400 MHz, CD₃OD) 0.74–0.85 (m, 6H), 0.99–1.26 (m, 4H), 1.38–1.65 (m, 10H), 3.27 (brs, 2H), 3.6–3.9 (m, 2H), 4.61 (s, 2H), 7.02 (brt, 1H), 7.09–7.17 (m, 3H), 7.31 (brt, 2H), 7.50 (s, 1H) | Meth 25 |
| 23[6] | (α-methyl tryptophan derivative with -NHC(O)CH₂O-Et) | Br | Et | (400 MHz, CD₃OD) 0.73–0.83 (m, 6H), 0.99–1.25 (m, 4H), 1.35–1.64 (m, 4H), 1.73 (s, 3H), 3.24 (brs, 2H), 3.40 (d, 1H), 3.55–3.85 (m, 3H), 4.45 (ABq, 2H), 6.90 (t, 1H), 6.95–7.04 (m, 3H), 7.06 (s, 1H), 7.10 (brd, 2H), 7.23 (d, 1H), 7.30 (brt, 2H), 7.41 (s, 1H), 7.53 (d, 1H) | Meth 26 |
| 24[5] | (cyclohexylmethyl amino acid with -NHC(O)CH₂O-Et) | Br | Et | (400 Mhz, CD₃OD) 0.75–1.9 (m, 27H), 3.27 (brs, 2H), 3.6–3.9 (m, 2H), 4.55 (dd, 1H), 4.70 (ABq, 2H), 7.03 (t, 1H), 7.10–7.18 (m, 3H), 7.31 (brt, 2H), 7.53 (s, 1H) | Meth 27 |
| 25[5] | (valine derivative with -NHC(O)CH₂O-Et) | Br | Et | (400 MHz, CD₃OD) 0.73–0.83 (m, 6H), 0.98 (t, 6H), 1.0–1.27 (m, 4H), 1.38–1.65 (m, 4H), 2.20–2.32 (m, 1H), 3.27 (brs, 2H), 3.6–3.9 (m, 2H), 4.47 (d, 1H), 4.73 (s, 2H), 7.03 (t, 1H), 7.10–7.16 (m, 3H), 7.31 (t, 2H), 7.53 (s, 1H) | Meth 28 |
| 26[5] | (histidine derivative with -NHC(O)CH₂O-Et) | Br | Et | (400 MHz, CD₃CN) 0.73–0.83 (m, 6H), 0.98–1.63 (m, 8H), 3.14 (dd, 1H), 3.23 (brs, 2H), 3.41 (dd, 1H), 3.57–3.8 (m, 2H), 4.66 (ABq, 2H), 4.88–4.95 (m, 1H), 6.99 (t, 1H), 7.08 (d, 2H), 7.16 (s, 1H), 7.20 (s, 1H), 7.29 (t, 2H), 7.41 (s, 1H), 7.73 (brd, NH), 8.40 (s, 1H) | Meth 29 |

-continued

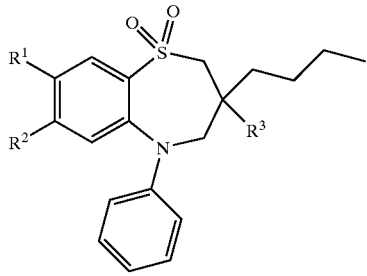

| Ex | R¹ | R² | R³ | NMR | SM |
|---|---|---|---|---|---|
| 27[5] | (1-methylimidazol-4-yl)methyl-CH(COOH)-NH-C(=O)-CH₂-O-CH(CH₃)₂ amino acid group | Br | Et | (400 MHz, CD₃CN) 0.73–0.83 (m, 6H), 0.98–1.63 (m, 8H), 3.14 (dd, 1H), 3.23 (brs, 2H), 3.37 (dd, 1H), 3.6–3.8 (m, 5H), 4.68 (ABq, 2H), 4.82–4.91 (m, 1H), 6.99 (t, 1H), 7.07 (d, 2H), 7.14 (s, 1H), 7.16 (s, 1H), 7.29 (t, 2H), 7.40 (s, 1H), 7.86 (brd, NH), 8.30 (s, 1H) | Meth 30 |
| 28[5] | O-tert-butyl threonine derivative | Br | Et | (400 MHz, CD₃CD) 0.75–0.84 (m, 6H), 1.0–1.33 (m, 16H), 1.33–1.65 (m, 4H), 3.28 (brs, 2H), 3.55–3.95 (m, 2H), 4.33–4.40 (m, 1H), 4.44 (d, 1H), 4.75 (d, 2H), 7.03 (t, 1H), 7.11–7.16 (m, 3H), 7.31 (brt, 2H), 7.55 (s, 1H) | Meth 31 |
| 29[5] | methionine derivative | Br | Et | (400 MHz, CD₃CD) 0.73–0.85 (m, 6H), 0.98–1.3 (m, 4H), 1.36–1.64 (m, 4H), 1.98–2.10 (m, 4H), 2.12–2.26 (m, 1H), 2.46–2.61 (m, 2H), 3.28 (brs, 2H), 3.6–2.9 (m, 2H), 4.63–4.77 (m, 3H), 7.02 (t, 1H), 7.09–7.17 (m, 3H), 7.31 (t, 2H), 7.52 (s, 1H) | Meth 32 |
| 30[5] | isoleucine derivative | Br | Et | (400 MHz, CD₃CD) 0.74–0.85 (m, 6H), 0.89–1.35 (m, 11H), 1.35–1.65 (m, 5H), 1.92–2.04 (m, 1H), 3.28 (brs, 2H), 3.6–3.9 (m, 2H), 4.49–4.54 (m, 1H), 4.72 (s, 2H), 7.03 (t, 1H), 7.08–7.18 (m, 3H), 7.31 (brt, 2H), 7.52 (s, 1H) | Meth 33 |
| 31[5] | cyclohexylmethyl amino acid derivative | Br | Et | (400 MHz, CD₃CD) 0.73–1.9 (m, 27H), 3.27 (brs, 2H), 3.6–3.9 (m, 2H), 4.55 (dd, 1H), 4.70 (ABq, 2H), 7.03 (t, 1H), 7.10–7.17 (m, 3H), 7.31 (brt, 2H), 7.53 (s, 1H) | Meth 34 |
| 32[5] | valine derivative | Br | Et | (400 Mhz, CD₃CD) 0.73–0.88 (m, 6H), 0.92–1.3 (m, 10H), 1.3–1.65 (m, 4H), 2.20–2.32 (m, 1H), 3.28 (brs, 2H), 3.6–3.9 (m, 2H), 4.47 (d, 1H), 4.73 (s, 2H), 7.03 (t, 1H), 7.10–7.17 (m, 3H), 7.31 (brt, 2H), 7.53 (s, 1H) | Meth 35 |

-continued

| Ex | R¹ | R² | R³ | NMR | SM |
|---|---|---|---|---|---|
| 33[5] | (histidine-derived substituent: imidazole-CH₂-CH(COOH)-NH-C(O)-CH₂-O-iPr) | Br | Et | (400 Mhz, CD₃CN) 0.73–0.84 (m, 6H), 0.96–1.63 (m, 8H), 3.14 (dd, 1H), 3.24 (brs, 2H), 3.40 (dd, 1H), 3.56–3.81 (m, 2H), 4.66 (ABq, 2H), 4.87–4.94 (m, 1H), 6.99 (t, 1H), 7.07 (d, 2H), 7.17 (s, 1H), 7.19 (s, 1H), 7.29 (t, 2H), 7.41 (s, 1H), 7.73 (brd, NH), 8.36 (brs, 1H) | Meth 36 |
| 34[5] | (cyclohexyl-CH(COOH)-NH-C(O)-CH₂-O-iPr) | MeS | n-Bu | (400 MHz, CD₃OD) 0.75–0.85 (m, 6H), 0.97–1.94 (m, 23H), 2.18 (s, 3H), 3.25 (brs, 2H), 3.6–3.9 (m, 2H), 4.33 (d, 1H), 4.67 (ABq, 2H), 6.71 (s, 1H), 6.98 (t, 1H), 7.12 (brd, 2H), 7.28 (t, 2H), 7.41 (s, 1H) | Meth 37 |
| 35[5] | (cyclohexyl-CH(COOH)-NH-C(O)-CH₂-O-iPr) | MeO | n-Bu | (400 MHz, CD₃OD): δ 0.75–0.85 (m, 6H), 0.96–1.91 (m, 23H), 3.22 (brs, 2H), 3.6–3.9 (m, 5H), 4.33 (d, 1H), 4.59 (d, 2H), 6.51 (s, 1H), 6.98 (t, 1H), 7.13 (brd, 2H), 7.28 (t, 2H), 7.52 (s, 1H) | Meth 38 |

[1] The compound was not purified.
[2] 1.9 eq LiOH and no purification.
[3] 7.6 eq of LiOH, added in portions, total reaction time approximately 6 hours.
[4] 4 eq LiOH.
[5] Extracted with DCM, no further purification.
[6] 8 eq of LiOH, reaction time was 5 days and then extracted with DCM, no further purification.

EXAMPLE 36

1,1-Dioxo-3-butyl-3-ethyl-5phenyl-7-bromo-8-{N-R-[1-carboxy-2-phenylethyl]carbamoylmethoxy}-2,3,4,5-tetrahydro-1,5-benzothiazepine 1,1-Dioxo-3-butyl-3-ethyl-5-phenyl-7-bromo-8-{N-R-[1-t-butoxycarbonyl-2-phenylethyl]carbamoylmethoxy}-2,3,4,5-tetrahydro-1,5-benzothiazepine (Method 17; 47 mg, 0.066 mmol) was dissolved in DCM (4 ml). TFA (1 ml) was added and the mixture was stirred at room temperature for 1 hour and 15 minutes. The reaction mixture was evaporated at reduced pressure. The residue was purified by preparative HPLC using an MeCN/ammonium acetate buffer gradient (5/95 to 100/0) as eluent. The fraction with the product was concentrated and then acidified with HCl-solution (aq, 2M). The water-layer was extracted twice with EtOAc. The combined organic layer was washed once with brine, dried, filtered and evaporated under reduced pressure to yield 31 mg (72%) of the title compound. NMR (400 MHz, CD₃OD) 0.74–0.83 (m, 6H), 1.0–1.27 (m, 4H), 1.36–1.65 (m, 4H), 3.08–3.3 (m, 4H), 3.54–3.92 (m, 2H), 4.09 (ABq, 2H), 4.78–4.88 (m, 1M), 7.03 (t, 1H), 7.1–7.34 (m, 9H), 7.49 (s, 1H), 7.79 (brd, NH).

EXAMPLES 37–38

The following compounds were synthesised from the appropriate starting materials by the procedure of Example 36.

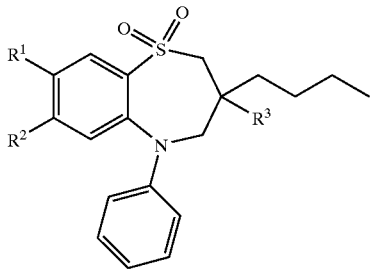

| Ex | R¹ | R² | R³ | NMR | SM |
|---|---|---|---|---|---|
| 37 | (benzyl-substituted hydroxy-carboxy-amide structure) | MeO | Et | (400 MHz, $CD_3OD$) 0.73–0.94 (m, 6H), 0.99–1.34 (m, 4H), 1.37–1.69 (m, 4H), 3.06–3.28 (m, 4H), 3.45–3.95 (m, 5H), 4.53 (ABq, 2H), 4.75–4.9 (m, 1H), 6.45 (s, 1H), 6.99 (t, 1H), 7.1–7.37 (m, 9H), 7.51 (s, 1H), 8.03 (brd, NH) | Meth 18 |
| 38[1] | (isobutyl-substituted hydroxy-carboxy-amide structure) | Br | Et | (400 MHz, $CD_3OD$) 0.73–0.86 (m, 6H), 0.90–1.27 (m, 10H), 1.39–1.65 (m, 4H), 1.65–1.78 (m, 3H), 3.27 (brs, 2H), 3.55–3.92 (m, 2H), 4.5–4.6 (m, 1H), 4.71 (ABq, 2H), 7.02 (brt, 1H), 7.1–7.17 (m, 3H), 7.31 (brt, 2H), 7.52 (s, 1H) | Meth 20 |

[1] 3 ml DCM:TFA 3:1

EXAMPLE 39

1,1-Dioxo-3-butyl-3-ethyl-5-phenyl-7-bromo-8-[N-(S-1-carboxy-2-R-hydroxypropyl)carbamoylmethoxy]-2,3,4,5-tetrahydro-1,5-benzothiazepine 1,1-Dioxo-3-butyl-3-ethyl-5-phenyl-7-bromo-8-[N-(S-1-carboxy-2-R-hybutoxypropyl)carbamoylmethoxy]-2,3,4,5-tetrahydro-1,5-benzothiazepine (Example 28; 18 mg, 0.027 mmol) was dissolved in TFA (1.5 ml). The mixture was stirred at room temperature for 4 hours. The reaction mixture was evaporated at reduced pressure. The residue was purified by preparative HPLC using an MeCN/ammonium acetate buffer gradient (5/95 to 100/0) as eluent. The fraction with the product was concentrated and then acidified with HCl-solution (aq, 2M). The water-layer was extracted twice with EtOAc. The combined organic layer was washed once with brine, dried, filtered and evaporated under reduced pressure to yield 11 mg (67%) of the title compound. NMR (400 MHz, $CD_3OD$) 0.73–0.95 (m, 6H), 0.95–1.35 (m, 7H), 1.35–1.66 (m, 4H), 3.28 (brs, 2H), 3.55–3.93 (m, 2H), 4.35–4.44 (m, 1H), 4.45–4.53 (m, 1H), 4.75 (s, 2H), 7.03 (brt 1H), 7.10–7.20 (m, 3H), 7.31 (brt, 2H), 7.55 (s, 1H).

Preparation of Starting Materials:

The starting materials for the Examples above are either commercially available or are readily prepared by standard methods from known materials. For example, the following reactions are an illustration, but not a limitation, of some of the starting materials used in the above reactions.

Method 1

1,1-Dioxo-3-butyl-3-ethyl-5-phenyl-7-(carboxymethoxy)-2,3,4,5-tetrahydro-1,5-benzothiazepine 1,1-Dioxo-3-butyl-3-ethyl-5-phenyl-7-(ethoxycarbonylmethoxy)-2,3,4,5-tetrahydro-1,5-benzothiazepine (Method 3; 110 mg, 0.24 mmol) and sodium hydroxide (100 mg, 2.5 mmol) were added to ethanol (5 ml, 95%). The mixture was refluxed for 1 h. AcOH (0.30 ml) was added and the reaction mixture was evaporated under reduced pressure. The residue was extracted with DCM/water. The DCM layer was separated, dried and evaporated under reduced pressure. The residue crystallised when treated with hexane. 82 mg (79%) of the title compound was obtained. NMR (500 MHz): 0.7–0.9 (m, 6H), 1.1–1.7 (m, 8H), 3.1–3.25 (m, 2H), 3.6–3.8 (br d, 2H), 4.6 (s, 2H), 6.9–7.1 (m, 5H), 7.2–7.3 (m, 2H),

Method 2

1,1-Dioxo-3-butyl-3-ethyl-5-phenyl-7-bromo-8-(carboxymethoxy)-2,3,4,5-tetrahydro-1,5-benzothiazepine The title compound was synthesised from 1,1-dioxo-3-butyl-3-ethyl-5-phenyl-7-bromo-8-(ethoxycarbonylmethoxy)-2,3,4,5-tetrahydro-1,5-benzothiazepine (Method 4) by the procedure of Method 1. NMR (500 MHz): 0.7–0.8 (m, 6H), 1.0–1.7 (m, 8H), 3.1–3.2 (m, 2H), 3.6 (brs, 2H), 4.6 (s, 2H), 6.9–7.1 (m, 4H), 7.2 (m, 2H), 7.5 (s, 1H).

Method 3

1,1-Dioxo-3-butyl-3-ethyl-5-phenyl-7-(ethoxycarbonylmethoxy)-2,3,4,5-tetrahydro-1,5-benzothiazepine 1,1-Dioxo-3-butyl-3-ethyl-5-phenyl-7-hydroxy-2,3,4,5-tetrahydro-1,5-benzothiazepine (WO 96/16051; 100 mg, 0.27 mmol), ethyl bromoacetate (50 mg, 0.30 mmol), sodium carbonate (100 mg, 0.94 mmol) and tetrabutylammonium bromide (10 mg 0.031 mmol) were added to MeCN (4 ml). The mixture was refluxed for 20 h and then evaporated under reduced pressure. The residue was purified by column chromatography on silica gel. The product was eluted with DCM: ethyl acetate (50:50). 120 mg (97%) of the title compound was obtained. NMR (300 MHz): 0.7–0.9 (m, 6H), 1.0–1.8 (m, 11H), 3.1–3.25 (m, 2H), 3.6–3.8 (m, 2H), 4.3 (q, 2H), 4.6 (s, 2H), 6.9–7.1 (m, 5H), 7.2–7.3 (m, 2H), 7.5 (d, 1H).

Method 4

1,1-Dioxo-3-butyl-3-ethyl-5-phenyl-7-bromo-8-(ethoxycarbonylmethoxy)-2,3,4,5-tetrahydro-1,5-benzothiazepine The title compound was synthesised from 1,1-dioxo-3-butyl-3-ethyl-5-phenyl-7-bromo-8-hydroxy-2,3,4,5-tetrahydro-1,5-benzothiazepine (WO 96/16051) by the procedure of Method 3. NMR (500 MHz): 0.7–0.9 (m, 6H), 1.0–1.8 (m, 11H), 3.2 (m, 2H), 3.6–3.8 (brs, 2H), 4.3 (q, 2H), 4.7 (s, 2H), 7.0–7.1 (m, 3H), 7.15 (s, 1H), 7.3 (m, 2H), (s, 1H).

Method 5

1,1-Dioxo-3-butyl-3-ethyl-5-phenyl-7-[N-(t-butoxycarbonylmethyl)carbamoylmethoxy]-2,3,4,5-tetrahydro-1,5-benzothiazepine 1,1-Dioxo-3-butyl-3-ethyl-5-phenyl-7-(carboxymethoxy)-2,3,4,5-tetrahydro-1,5-benzothiazepine (Method 1; 66 mg, 0.15 mmol), glycine-t-butyl ester hydrochloride (30 mg, 0.18 mmol) and triethylamine (100 mg, 0.99 mmol) were dissolved in DCM (2 ml). The mixture was stirred for 5 min at room temperature. TBTU (60 mg, 0.19 mmol) was added and the mixture was stirred for 1 h at room temperature. The solvent was evaporated at reduced pressure and the residue was placed on a silica column and the product was eluted with DCM/methanol (95:5). 80 mg (96%) of the title compound was obtained. NMR (500 MHz): 0.7–0.9 (m, 6H), 1.1–1.7 (m, 17H), 3.1–3.3 (m, 2H), 3.6–3.8 (br d, 2H), 4.0 (d, 2H), 6.9–7.1 (m, 6H), 7.2–7.3 (m, 2H), 7.6 (d, 1H).

Methods 6–13

The following compounds were synthesised from 1,1-dioxo-3-butyl-3-ethyl-5-phenyl-7-bromo-8-(carboxymethoxy)-2,3,4,5-tetrahydro-1,5-benzothiazepine (Method 2), 1,1-dioxo-3,3-dibutyl-5-phenyl-7-bromo-8-carboxymethoxy-2,3,4,5-tetrahydro-1,5-benzothiazepine Method 42) or 1,1-dioxo-3-butyl-3-ethyl-5-phenyl-7-bromo-8-(1-carboxyethoxy)-2,3,4,5-tetrahydro-1,5-benzothiazepine (Method 40) by the procedure of Method 5.

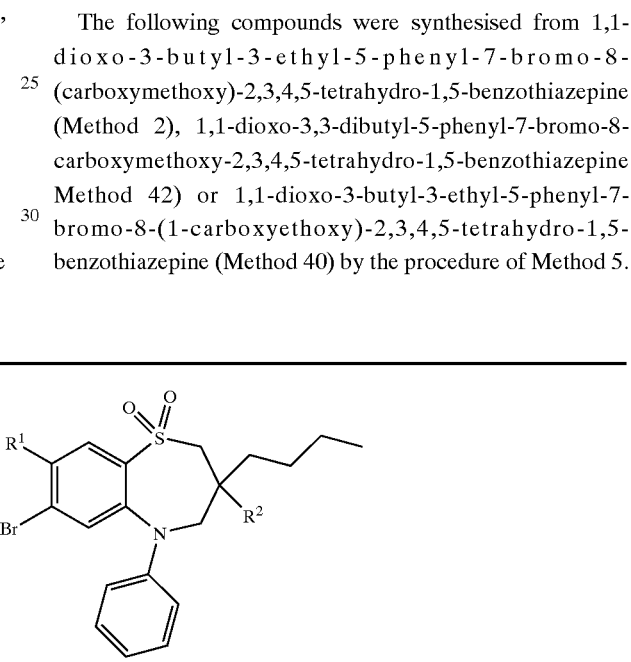

| Method | R¹ | R² | NMR/M/z |
|---|---|---|---|
| 6 | ![structure] | Et | 500 MHz: 0.7–0.8 (m, 6H), 1.0–1.7 (m, 17H), 3.2 (m, 2H), 3.7 (brs, 2H), 4.1 (d, 2H), 4.6 (s, 2H), 7.0–7.1 (m, 3H), 7.15 (s, 1H), 7.3 (m, 2H), 7.5 (s, 1H) |
| 7 | ![structure] | Et | 300 MHz: 0.7–0.8 (m, 6H), 1–1.7 (m, 14H), 2–2.5 (m, 4H), 3.2 (m, 2H), 3.8 (brs, 2H), 4.1 (q, 2H), 4.2 (q, 2H), 4.6 (dd, 2H), 4.8 (m, 1H), 7–7.15 (m, 4H), 7.3 (m, 2H), 7.4 (d, 1H), 7.5 (s, 1H) |

-continued
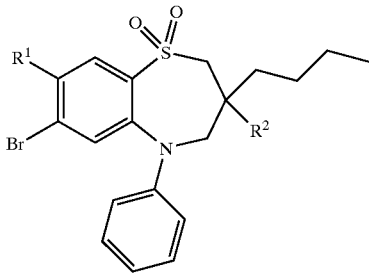
| Method | R¹ | R² | NMR/M/z |
|---|---|---|---|
| 8 | (3-pyridylmethyl, methyl ester, NH-C(O)-CH2-O-Et) | Et | m/z = 673.3 |
| 9 | (ethyl ester, CH2-NH-C(O)-CH(CH3)-O-Et) | Et | m/z = 610.2 |
| 10 | (ethyl ester, CH2-N(Bn)-C(O)-CH2-O-Et) | Et | m/z = 686.3 |
| 11 | HO-(4-hydroxybenzyl, t-Bu ester, NH-C(O)-CH2-O-Et) | Et | m/z = 730.1 |
| 12 | HO-(4-hydroxybenzyl, t-Bu ester, NH-C(O)-CH2-O-Et) | n-Bu | m/z = 758.0 |
| 13 | (t-Bu ether serine, t-Bu ester, NH-C(O)-CH2-O-Et) | n-Bu | (400 MHz) 0.6–0.8 (m, 6H), 1.0–1.6 (m, 30H), 3.19 (m, 2H), 3.5–3.9 (m, 4H), 4.5–4.7 (m, 3H), 7.0–7.1 (m, 4H), 7.3–7.4 (m, 2H), 7.5 (s, 1H), 7.6 (d, 1H) |

Method 14

1,1-Dioxo-3-butyl-3-ethyl-5-phenyl-7-bromo-8-[N-S-(1-ethoxycarbonyl-2-phenylethyl)carbamoylmethoxy]-2,3,4,5-tetrahydro-1,5-benzothiazepine 1,1-dioxo-3-butyl-3-ethyl-5-phenyl-7-bromo-8-(carboxymethoxy)-2,3,4,5-tetrahydro-1,5-benzothiazepine (Method 2; 71.7 mg, 0.14 mmol) was dissolved in DCM (2 ml) methyl L-phenylalaninate (36 mg, 0.17 mmol) and DIPEA (0.097 ml, 0.56 mmol) was added and the reaction was stirred for 2 minutes. TBTU (54.3 mg, 0.17 mmol) was added and the mixture was stirred for 30 minutes at room temperature. The mixture was evaporated at reduced pressure. The product was purified using an ISOLUTE column eluting with DCM/ethyl acetate 8/2. 92 mg (97%) of the title compound was obtained. M/z 671.7.

Methods 1–38

The following compounds were synthesised from the appropriate starting materials by the procedure of Method 14.

| Meth | R¹ | R² | R³ | NMR/M/z | SM |
|---|---|---|---|---|---|
| 15 | (isobutyl-CH-COOMe-NH-C(O)-CH₂-O-) | Br | Et | m/z 637.6 | Meth 2 |
| 16[1] | (indol-3-yl-CH₂-CH-COOMe-NH-C(O)-CH₂-O-) | Br | Et | m/z 710.7 | Meth 2 |
| 17[2] | (benzyl-CH-COOtBu-NH-C(O)-CH₂-O-) | Br | Et | m/z 713.7 | Meth 2 |
| 18 | (benzyl-CH-COOtBu-NH-C(O)-CH₂-O-) | MeO | Et | m/z 664.9 | Meth 48 |

-continued

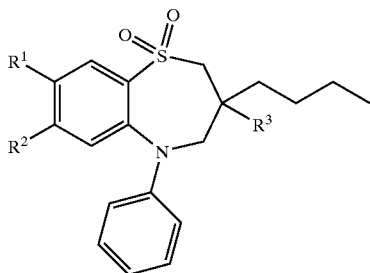

| Meth | R¹ | R² | R³ | NMR/M/z | SM |
|---|---|---|---|---|---|
| 19[4] | (methyl phenylalaninate with NH-C(O)-CH2-O-Et group) | MeO | Et | m/z 622.8 | Meth 48 |
| 20[5] | (tert-butyl leucinate with NH-C(O)-CH2-O-Et group) | Br | Et | m/z 679.7 | Meth 2 |
| 21[6] | (methyl tryptophanate with NH-C(O)-CH2-O-Et group) | Br | Et | m/z 710.7 | Meth 2 |
| 22[6] | (ethyl alaninate with NH-C(O)-CH2-O-Et group) | Br | Et | m/z 609.6 | Meth 2 |
| 23[7] | (methyl alaninate with NH-C(O)-CH2-O-Et group) | Br | Et | m/z 595.6 | Meth 2 |
| 24[2] | (methyl 1-aminocyclopropanecarboxylate with NH-C(O)-CH2-O-Et group) | Br | Et | m/z 607.6 | Meth 2 |
| 25[8] | (methyl 2-aminoisobutyrate with NH-C(O)-CH2-O-Et group) | Br | Et | m/z 609.6 | Meth 2 |

-continued
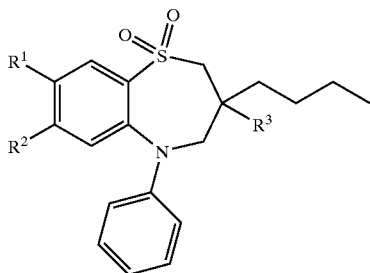
| Meth | R¹ | R² | R³ | NMR/M/z | SM |
|---|---|---|---|---|---|
| 26[8] | 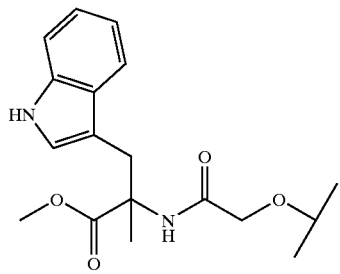 | Br | Et | m/z 724.7 | Meth 2 |
| 27[8] | 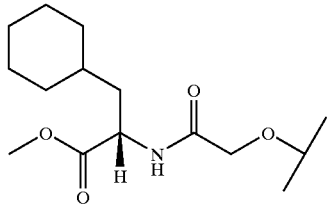 | Br | Et | m/z 677.7 | Meth 2 |
| 28[8] | 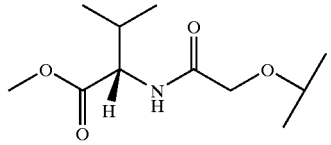 | Br | Et | m/z 623.6 | Meth 2 |
| 29[9] | 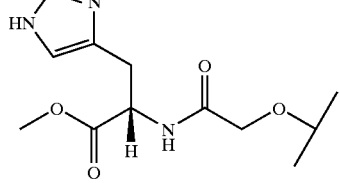 | Br | Et | m/z 661.6 | Meth 2 |
| 30[9] | 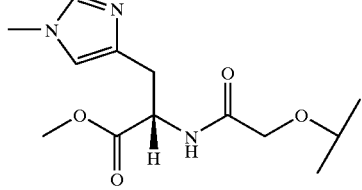 | Br | Et | m/z 675.6 | Meth 2 |
| 31[8] | 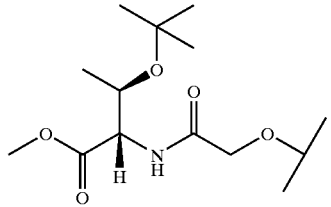 | Br | Et | m/z 681.7 | Meth 2 |

-continued

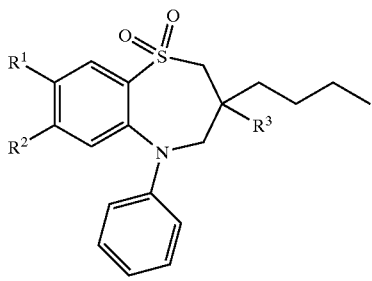

| Meth | R¹ | R² | R³ | NMR/M/z | SM |
|---|---|---|---|---|---|
| 32[8] | (methyl ester, methionine-like, with OCH₂-O-ethyl amide) | Br | Et | m/z 656.7 | Meth 2 |
| 33[2] | (methyl ester, isoleucine-like, with OCH₂-O-ethyl amide) | Br | Et | m/z 637.6 | Meth 2 |
| 34[8] | (methyl ester, cyclohexylalanine-like, with OCH₂-O-ethyl amide) | Br | Et | m/z 677.7 | Meth 2 |
| 35[8] | (methyl ester, valine-like, with OCH₂-O-ethyl amide) | Br | Et | m/z 623.6 | Meth 2 |
| 36[9] | (methyl ester, histidine-like, with OCH₂-O-ethyl amide) | Br | Et | m/z 661.6 | Meth 2 |
| 37[8,10] | (methyl ester, cyclohexylglycine-like, with OCH₂-O-ethyl amide) | MeS | n-Bu | m/z 658.9 | Meth 44 |

-continued

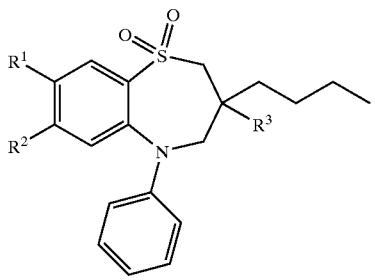

| Meth | R¹ | R² | R³ | NMR/M/z | SM |
|---|---|---|---|---|---|
| 38[8,10] | (cyclohexyl glycine methyl ester ethoxyacetamide structure) | MeO | n-Bu | m/z 642.7 | Meth 46 |

[1] Reaction time 40 minutes.
[2] Reaction time 1.5 hours.
[3] Reaction time 2 hours and chromatographed twice.
[4] 1.3 eqv amino acid, TBTU 1.3 eqv and eluted first with DCM then DCM:EtOAc 9:1 to 8:2.
[5] Reaction time 45 minutes and eluted first with DCM then DCM:EtOAc 9:1 to 8:2.
[6] Reaction time 1 hour and eluted first with DCM then DCM:EtOAc 9:1 to 8:2.
[7] Reaction time 40 minutes and eluted first with DCM then DCM:EtOAc 9:1 to 8:2.
[8] Reaction time overnight.
[9] Reaction time overnight and the product was eluted with EtAC:MeOH (saturated with NH₃) 9:1
[10] Amine: Justus Liebigs Ann. Chem.; 523; 1936; 199

Method 39

1,1-Dioxo-3-butyl-3-ethyl-5-phenyl-7-bromo-8-(1-ethoxycarbonylethoxy)-2,3,4,5-tetrahydro-1,5-benzothiazepine Sodium carbonate (0.30 g, 2.83 mmol), 2-bromopropanoic acid ethyl ester (0.145 g, 0.796 mmol) and tetrabutylammonium bromide (0.022 g, 0.07 mmol) was added to a solution of 1,1-dioxo-3-butyl-3-ethyl-5-phenyl-7-bromo-8-hydroxy-2,3,4,5-tetrahydro-1,5-benzothiazepine (WO 96/16051; 0.300 g, 0.663 mmol) in MeCN (10 ml). The suspension was heated under reflux over night. The solvent was evaporated and the crude mixture was extracted (DCM/H$_2$O), dried (MgSO$_4$), evaporated and purified by flash chromatography (Hex:EtOAc-5:1) to give the title compound 0.346 g (95%) as a white solid. NM (400 MHz) 0.70–0.85 (m, 6H), 1.00–1.75 (m, 8H), 1.35 (t, 3H), 1.70 (d, 3H), 3.05–3.25 (m, 2H), 3.55–3.90 (m, 2H), 4.20–4.35 (m, 2H), 4.80 (q, 1H), 7.00–7.10 (m, 3H), 7.15 (s, 1H), 7.25–7.35 (m, 2H), 7.45 (s, 1H).

Method 40

1,1-dioxo-3-butyl-3-ethyl-5-phenyl-7-bromo-8-(-carboxyethoxy)-2,3,4,5-tetrahydro-1,5-benzothiazepine Sodium hydroxide (0.045 g, 1.13 mmol) was added to a solution of 1,1-dioxo-3-butyl-3-ethyl-5-phenyl-7-bromo-8-(1-ethoxycarbonylethoxy)-2,3,4,5-tetrahydro-1,5-benzothiazepine (Method 39; 0.050 g, 0.090 mmol) in EtOH (4 ml, 95%) and heated under reflux. After 1.5 hours AcOH (0.2 ml) was added and most of the solvent was removed under reduced pressure. The crude product was extracted (DCM/H$_2$), dried (MgSO$_4$) and evaporated to give the title compound 0.031 g (65%) as white solid. NMR (500 MHz, CD$_3$OD) 0.70–0.85 (m, 6H), 0.95–1.25 (m, 4H), 1.35–1.70 (m, 4H), 2.65 (d, 3H), 3.10–3.35 (m, 2H), 3.45–3.95 (m, 2H), 4.70 (q, 1H), 6.90–7.35 (m, 6H), 7.45 (s, 1H).

Method 41

1,1-Dioxo-3,3-dibutyl-5-phenyl-7-bromo-8-ethoxycarbonylmethoxy-2,3,4,5-tetrahydro-1,5-benzothiazepine 1,1-Dioxo-3,3-dibutyl-5-phenyl-7-bromo-8-hydroxy-2,3,4,5-tetrahydro-1,5-benzothiazepine (synthesised by the of WO9616051 for the corresponding 3-butyl-3-ethyl analogue; 2.0 g, 4.16 mmol), ethyl bromoacetate (0.84 g, 5.03 mmol), sodium carbonate (2.0 g, 18.9 mmol) and tetrabutylammonium bromide (80 mg, 0.25 mmol) were added to MeCN (20 ml). The mixture was refluxed for 2 hours and then evaporated under reduced pressure. The residue was extracted with DCM/water. The DCM layer was separated and evaporated under reduced pressure. The residue was purified by column chromatography on silica gel. The product was eluted with DCM/EtOAc (90:10) to give the title compound 2.2 g (93%). NMR (400 MHz) 0.7–0.8 (m, 6H), 1.0–1.6 (m, 15H), 3.2 (brs, 2H), 3.7 (brs, 2H), 4.3 (q, 2H), 4.7 (s, 2H), 7.0–7.3 (m, 6H), 7.4 (s, 1H).

Method 42

1,1-Dioxo-3,3-dibutyl-5-phenyl-7-bromo-8-carboxymethoxy-2,3,4,5-tetrahydro-1,5-benzothiazepine 1,1-Dioxo-3,3-dibutyl-5-phenyl-7-bromo-8-ethoxycarbonylmethoxy-2,3,4,5-tetrahydro-1,5- benzothiazepine (Method 41; 2.2 g, 3.88 mmol) was dissolved in ethanol (15 ml). NaOH (0.8 g in 1.5 ml water) was added to the solution and the mixture was stirred for 30 min at room temperature. AcOH (2 ml) was added. The solvent was evaporated under reduced pressure and the residue was extracted with EtOAc/water. The EtOAc layer was separated, dried and evaporated under reduced pressure to give the title compound 2.0 g (95%). NMR (500 MHz) 0.7–0.8 (m, 6H), 1.0–1.5 (m, 12H), 3.2 (brs, 2H), 3.7 (brs, 2H), 4.7 (s, 2H), 7.0–7.3 (m, 6H), 7.4 (s, 1H).

Method 43

1,1-Dioxo-3-butyl-3-ethyl-5-phenyl-7-methylthio-8-ethoxycarbonylmethoxy-2,3,4,5-tetrahydro-1,5-benzothiazepine To 1,1-dioxo-3-butyl-3-ethyl-5-phenyl-7-methylthio-8-hydroxy-2,3,4,5-tetrahydro-1,5-benzothiazepine Method 49; 500 mg, 1.2 mmol) was added MeCN (30 ml), tetrabutylammonium bromide (30 mg, 0.08 mmol), anhydrous sodium carbonate (500 mg, 4.7 mmol), ethyl bromoacetate (0.14 ml, 1.26 mmol) and caesium carbonate (20 mg, 0.06 mmol). This reaction mixture was then stirred over night at 80° C. Then the solvent was removed under reduced pressure, water and DCM were added and the aqueous phase was extracted three times with DCM. The combined organic phases were then dried, concentrated and purified by flash chromatography [DCM: EtOAc, 1:0, 9:1] to give the title compound 600 mg (99%). NMR (300 MHz) 0.8–1.0 (m, 6, 1.0–1.8 (m, 1H), 2.2 (s, 3H), 3.2 (q, 2H), 3.75 (brq, 2H), 4.3 (q, 2), 4.75 (s, 1H), 6.7 (s, 1H), 6.95 (t, 1H), 7.05 (d, 2H), 7.25 (t, 2H), 7.3 (s, 1H).

Method 44

1,1-Dioxo-3-butyl-3-ethyl-5-phenyl-7-ethylthio-8-carboxymethoxy-2,3,4,5-tetrahydro-1,5-benzothiazepine 1,1-Dioxo-3-butyl-3-ethyl-5-phenyl-7-methylthio-8-ethoxycarbonylmethoxy-2,3,4,5 tetrahydro-1,5-benzothiazepine (Method 43; 478 mg, 0.95 mmol) was added THF (15 ml), water (3 ml) and LiOH (34 mg, 1.4 mmol). The reaction was then stirred for 1 hour. Then AcOH (0.2 ml) was added along with water (10 ml) and DCM (10 ml) The aqueous layer was then extracted three times with DCM. The combined organic phases were then dried and concentrated to give the title compound 450 mg (99%). NMR (400 MHz) 0.7–0.9 (m, 6H), 1.0–1.7 (m, 8H), 2.2 (s, 3H), 3.2 (q, 2H), 3.7 (m, 2H), 4.8 (s, 2H), 6.65 (s, 1H), 0–7.9 (m, 6H), 7.05 (d, 2H), 7.25 (t, 2H), 7.35 (s, 1H), 8.4 (brs, 1H).

Method 45

1,1-Dioxo-3,3-dibutyl-5-phenyl-7-methoxy-8-ethoxycarbonylmethoxy-2,3,4,5-tetrahydro-1,5-benzothiazepine Ethyl bromoacetate (0.13 ml), $Na_2CO_3$ (0.40 g) and tetrabutylammonium bromide (0.030 g) were added to a solution of 1,1-dioxo-3,3-dibutyl-5-phenyl-7-methoxy-8-hydroxy-2,3,4,5-tetrahydro-1,5-benzothiazepine (synthesised by the of WO9616051 for the corresponding 3-butyl-3-ethyl analogue; 0.400 g, 0.927 mmol) in MeCN (10 ml). The suspension was heated under reflux overnight before most of the solvent was removed under reduced pressure. The crude product was extracted (DCM/$H_2O$) and filtered through a short silica-column (DCM:EtOAc-1:4) to give the title compound 0.476 g (99%). NMR (400 MHz 0.65–0.85 (m, 6H), 0.95–1.65 (m, 8H), 3.00–3.15 (m, 2H), 3.50–3.80 (m, 2H), 3.70–3.80 (s, 3H), 5.60 (s, 1H), 5.65 (d, 1H), 7.00–7.60 (m, 17H), 8.05–8.20 (d, 1H).

Method 46

1,1-Dioxo-3,3-dibutyl-5-phenyl-7-methoxy-8-carboxymethoxy-2,3,4,5-tetrahydro-1,5-benzothiazepine Lithium hydroxide (0.062 g) was added to a solution of 1,1-dioxo-3,3-dibutyl-5-phenyl-7-methoxy-8-ethoxycarbonylmethoxy-2,3,4,5-tetrahydro-1,5-benzothiazepine (Method 45; 0.448 g, 0.865 mmol) in THF/$H_2O$ (2/1, 6 ml). After 1 hour AcOH (0.5 ml) was added and most of the solvent was removed under reduced pressure. The crude product was purified by HPLC (MeCN) to give the title compound 0.408 g (96%) as a white solid. NMR (400 MHz, $CD_3OD$): 0.75–0.85 (m, 6H), 1.00–1.30 (m, 8H), 1.35–1.55 (m, 4H), 3.20 (s, 2H), 3.65 (s, 3H), 3.70 (brs, 2H), 4.50 (s, 2H), 6.50 (s, 1H), 6.90–7.30 (m, 5H),

Method 47

1,1-Dioxo-3-butyl-3-ethyl-5-phenyl-7-methoxy-8-ethoxycarbonylmethoxy-2,3,4,5-tetrahydro-1,5-benzothiazepine 1,1-dioxo-3-butyl-3-ethyl-5-phenyl-7-methoxy-8-hydroxy-2,3,4,5-tetrahydro-1,5-benzothiazepine (WO 9616051; 1.0 g), ethyl bromoacetate (0,50 g), sodium carbonate (1.2 g) and tetrabutylammonium bromide (60 mg) in MeCN (15 ml) were refluxed over night. The solvent was removed under reduced pressure and the residue was extracted (DCM/$H_2O$). The organic layer was separated and the solvent was removed under reduced pressure. The residue purified by chromatography (DCM/EtOAc (90:10)) to give the title compound 1.2 g (98%). NMR (400 MHz, $CD_3OD$) 0.75–0.85 (m, 6H), 1.00–1.30 (m, 8H), 1.35–1.55 (m, 4H), 3.20 (s, 2H), 3.65 (s, 3H), 3.70 (brs, 2H), 4.50 (s, 2H), 6.50 (s, 1H), 6.90–7.30 (m,5H), 7.40 (s, 1H).

Method 48

1,1-Dioxo-3-butyl-3-ethyl-5-phenyl-7-methoxy-8-carboxymethoxy-2,3,4,5-tetrahydro-1,5-benzothiazepine 1,1-Dioxo-3-butyl-3-ethyl-5-phenyl-7-methoxy-8-ethoxycarbonylmethoxy-2,3,4,5-tetrahydro-1,5-benzothiazepine (Method 47; 1.2 g) was dissolved in ethanol (20 ml). Sodium hydroxide (0.5) dissolved in $H_2O$ (1 ml) was added and the reaction mixture was warmed to 40° C. for 30 min. AcOH (1 ml) was added and the solvent was removed at reduced pressure. The residue was partitioned between DCM/$H_2O$ and the organic layer was separated and dried. Trituration of the residue with n-hexane gave the title compound 1.1 g (97%) as a solid. NMR (400 MHz; $CDCl_3$): 0.75–0.85 (m, 3H), 0.9 (t, 3H), 1.0–1.7 (m, 8H), 3.2 (q, 2H), 3.65 (s, 3H), 3.65–3.85 (m, 2H), 4.7 (s, 2H), 6.4 (s, 1H), 7.0 (t, 1H), 7.1 (d, 2H), 7.3 (t, 2H), 7.5 (s, 1H).

Method 49

1,1-Dioxo-3-butyl-3-ethyl-5-phenyl-7-methylthio-8-hydroxy-2,3,4,5-tetrahydro-1,5-benzothiazepine To 1,1-dioxo-3-butyl-3-ethyl-5-phenyl-7-bromo-8-methoxy-2,3,4,5-tetrahydro-1,5-benzothiazepine (WO9616051; 600 mg, 1.29 mmol) were added DMF (5 ml) and sodium methanethiolate (450 mg, 6.42 mmol). The reaction was then heated to 60° C. for 1 hour. The oil bath was then heated to 120° C. for 4 hours. To quench the reaction, the temperature was lowered to room temperature and excess acetic acid was added quickly. The reaction was kept under a flow of nitrogen through sodium hypochlorite for 2 hours. Water and EtOAc were added and the aqueous phase was extracted three times with EtOAc. The combined organic phases were washed with water, dried and concentrated under reduced pressure. The residue was then purified by flash chromatography [DCM: EtOAc, 9:1] to give the title compound 0.5 g (92%). NMR (400 MHz) 0.65–0.8 (m, 6H), 0.95–1.6 (m, 8H), 3.1 (q, 2H), 3.6 (brq, 2H), 6.75 (s, 1H), 6.8 (t, 1H), 6.9 (d, 2H), 7.15 (t, 2H), 7.55 (s, 1H).

Example 40

The following illustrate representative pharmaceutical dosage forms containing the compound of formula (I), or a pharmaceutically acceptable salt, solvate, solvate of such a salt or a prodrug thereof (hereafter compound X), for therapeutic or prophylactic use in humans

| (a): Tablet I | mg/tablet |
| --- | --- |
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b): Tablet II | mg/tablet |
| --- | --- |
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c): Tablet III | mg/tablet |
| --- | --- |
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d): Capsule | mg/capsule |
| --- | --- |
| Compound X | 10 |
| Lactose Ph.Eur | 488.5 |
| Magnesium stearate | 1.5 |

| (e): Injection I | (50 mg/ml) |
| --- | --- |
| Compound X | 5.0% w/v |
| 1 M Sodium hydroxide solution | 15.0% v/v |
| 0.1 M Hydrochloric acid | (to adjust pH to 7.6) |
| Polyethylene glycol 400 | 4.5% w/v |
| Water for injection | to 100% |

| (f): Injection II | 10 mg/ml |
| --- | --- |
| Compound X | 1.0% w/v |
| Sodium phosphate BP | 3.6% w/v |
| 0.1 M Sodium hydroxide solution | 15.0% v/v |
| Water for injection | to 100% |

| (g): Injection III | (1 mg/ml, buffered to pH 6) |
| --- | --- |
| Compound X | 0.1% w/v |
| Sodium phosphate BP | 2.26% w/v |

| -continued | |
| --- | --- |
| Citric acid | 0.38% w/v |
| Polyethylene glycol 400 | 3.5% w/v |
| Water for injection | to 100% |

Note
The above formulations may be obtained by conventional procedures well known in the pharmaceutical art. The tablets (a)–(c) may be enteric coated by conventional means, for example to provide a coating of cellulose acetate phthalate.

What we claim is:

1. A compound of formula (I):

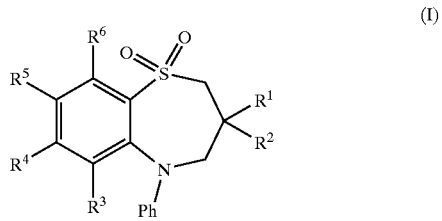

wherein:

$R^1$ and $R^2$ are independently selected from $C_{1-6}$alkyl;
one of $R^4$ and $R^5$ is a group of formula (IA):

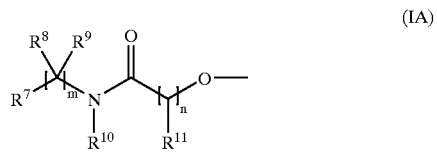

$R^3$ and $R^6$ and the other of $R^4$ and $R^5$ are independently selected from hydrogen, halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N-($C_{1-4}$alkyl)amino, N,N-($C_{1-4}$alkyl)$_2$amino, $C_{1-4}$alkanoylamino, N-($C_{1-4}$alkyl)carbamoyl, N,N-($C_{1-4}$alkyl)$_2$carbamoyl, $C_{1-4}$alkylS(O)$_a$ wherein a is 0 to 2, $C_{1-4}$alkoxycarbonyl, N-($C_{1-4}$alkyl)sulphamoyl and N,N-($C_{1-4}$alkyl)$_2$ sulphamoyl; wherein $R^3$ and $R^6$ and the other of $R^4$ and $R^5$ may be optionally substituted on carbon by one or more $R^{14}$;

$R^7$ is carboxy, sulpho, sulphino, phosphono, —P(O)(OR$^a$)(OR$^b$), P(O)(OH)(OR$_a$), —P(O)(OH)(R$^a$) or P(O)(OR$^a$)(R$^b$), wherein R$^a$ and R$^b$ are independently selected from $C_{1-6}$alkyl; or $R^7$ is a group of formula (IB):

$R^8$ and $R^9$ are independently hydrogen, $C_{1-4}$alkyl or a saturated cyclic group, or $R^8$ and $R^9$ together form $C_{2-6}$alkylene; wherein $R^8$ and $R^9$ or $R^8$ and $R^9$ together may be independently optionally substituted on carbon by one or more substituents selected from $R^{15}$; and wherein if said saturated cyclic group contains an —NH— moiety, that nitrogen may be optionally substituted by one or more $R^{20}$;

$R^{10}$ is hydrogen or $C_{1-4}$alkyl; wherein $R^{10}$ is optionally substituted on carbon by one or more substituents selected from $R^{24}$;

$R^{11}$ is hydrogen, $C^{1-4}$alkyl, carbocyclyl or heterocyclyl; wherein $R^{11}$ is optionally substituted on carbon by one or more substituents selected from $R^{16}$; and wherein if said heterocyclyl contains an —NH— moiety, that nitrogen may be optionally substituted by one or more $R^{21}$;

$R^{12}$ is hydrogen or $C_{1-4}$alkyl, carbocyclyl or heterocyclyl; wherein $R^{12}$ optionally substituted on carbon by one or more substituents selected from $R^{17}$; and wherein if said heterocyclyl contains an —NH— moiety, that nitrogen may be optionally substituted by one or more $R^{22}$;

$R^{13}$ is carboxy, sulpho, sulphino, phosphono, —P(O)(OR$^c$)(OR$^d$), —P(O)(OH)(OR$^c$), —P(O)(OH)(R$^c$) or —P(O)(OR$^c$)(R$^d$) wherein R$^c$ and R$^d$ are independently selected from $C_{1-6}$alkyl;

m is 1–3; wherein the values of $R^8$ and $R^9$ may be the same or different;

n is 1–3; wherein the values of $R^{11}$ may be the same or different;

p is 1–3; wherein the values of $R^{12}$ may be the same or different;

$R^{14}$ and $R^{16}$ are independently selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N-($C_{1-4}$alkyl)amino, N,N-($C_{1-4}$alkyl)$_2$amino, $C_{1-4}$alkanoylamino, N-($C_{1-4}$alkyl)carbamoyl, N,N-($C_{1-4}$ alkyl)$_2$carbamoyl, $C_{1-4}$alkylS(O)$_a$ wherein a is 0 to 2, $C_{1-4}$alkoxycarbonyl, N-($C_{1-4}$alkyl)sulphamoyl and N,N-($C_{1-4}$alkyl)$_2$sulphamoyl; wherein $R^{14}$ and $R^{16}$ may be independently optionally substituted on carbon by one or more $R^{18}$;

$R^{15}$ and $R^{17}$ are independently selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N-($C_{1-4}$alkyl)amino, N,N-($C_{1-4}$alkyl)$_2$amino, $C_{1-4}$alkanoylamino, N-($C_{1-4}$alkyl)carbamoyl, N,N-($C_{1-4}$ alkyl)$_2$carbamoyl, $C_{1-4}$alkylS(O)$_a$ wherein a is 0 to 2, $C_{1-4}$alkoxycarbonyl, N-($C_{1-4}$alkyl)sulphamoyl and N,N-($C_{1-4}$alkyl)$_2$sulphamoyl, carbocyclyl, heterocyclyl, sulpho, sulphino, amidino, phosphono, —P(O)(OR$^e$)(OR$^f$), —P(O)(OH)(OR$^e$), —P(O)(OH)(R$^e$) or —P(O)(OR$^e$)(R$^f$), wherein R$^e$ and R$^f$ are independently selected from $C_{1-6}$alkyl; wherein $R^{15}$ and $R^{17}$ may be independently optionally substituted on carbon by one or more $R^{19}$; and wherein if said heterocyclyl contains an —NH— moiety, that nitrogen may be optionally substituted by one or more $R^{23}$;

$R^{18}$, $R^{19}$ and $R^{25}$ are independently selected from halo, hydroxy, cyano, carbamoyl, ureido amino nitro, carboxy, carbamoyl, mercapto, sulphamoyl, trifluoromethyl, trifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl;

$R^{20}$, $R^{21}$, $R^{22}$, $R^{23}$ and $R^{26}$ are independently $C_{1-4}$alkyl, $C_{1-4}$alkanoyl, $C_{1-4}$alkylsulphonyl, sulphamoyl, N-($C_{1-4}$alkyl)sulphamoyl, N,N-($C_{1-4}$alkyl)$_2$sulphamoyl, $C_{1-4}$alkoxycarbonyl, carbamoyl, N-($C_{1-4}$alkyl)carbamoyl, N,N-($C_{1-4}$alkyl)$_2$carbamoyl, benzyl, phenethyl, benzoyl, phenylsulphonyl and phenyl;

$R^{24}$ is selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N-($C_{1-4}$alkyl)amino, N,N-($C_{1-4}$alkyl)$_2$ amino, $C_{1-4}$alkanoylamino, N-($C_{1-4}$alkyl)carbamoyl, N,N-($C_{1-4}$alkyl)$_2$carbamoyl, $C_{1-4}$alkylS(O)$_a$ wherein a is 0 to 2, $C_{1-4}$alkoxycarbonyl, N-($C_{1-4}$alkyl)sulphamoyl and N,N-($C_{1-4}$alkyl)$_2$sulphamoyl, carbocyclyl, heterocyclyl; wherein $R^{24}$ may be independently optionally substituted on carbon by one or more $R^{25}$; and wherein if said heterocyclyl contains an —NH— moiety, that nitrogen may be optionally substituted by one or more $R^{26}$;

wherein any saturated cyclic group is a totally or partially saturated, mono or bicyclic ring containing 3–12 atoms of which 0–4 atoms are chosen from nitrogen, sulphur or oxygen, which may be carbon or nitrogen linked;

wherein any heterocyclyl is a saturated, partially saturated or unsaturated, mono or bicyclic ring containing 3–12 atoms of which at least one atom is chosen from nitrogen, sulphur or oxygen, which may be carbon or nitrogen linked, wherein a —CH$_2$— group can optionally be replaced by a —C(O)— or a ring sulphur atom may be optionally oxidised to form the S-oxides; and wherein any carbocyclyl is a saturated, partially saturated or unsaturated, mono or bicyclic carbon ring that contains 3–12 atoms, wherein a —CH$_2$— group can optionally be replaced by a —C(O)—;

or a pharmaceutically acceptable salt thereof.

2. A compound of formula (I) according to claim 1 wherein $R^1$ and $R^2$ are independently selected from ethyl or butyl or a pharmaceutically acceptable salt thereof.

3. A compound of formula (I) according to claim 1 wherein $R^3$ is hydrogen or a pharmaceutically acceptable salt thereof.

4. A compound of formula (I) according to claim 1 wherein $R^5$ is a group of formula (IA) and $R^4$ is bromo, methoxy or methylthio or a pharmaceutically acceptable salt thereof.

5. A compound of formula (I) according to claim 1 wherein $R^5$ is N-(carboxymethyl)carbamoylmethoxy, N-(2-sulphoethyl)carbamoylmethoxy, N-(1,3-dicarboxypropyl)carbamoylmethoxy, N-(3-sulphopropyl)carbamoylmethoxy, N-[N-(2-sulphoethyl)carbamoylmethyl]carbamoylmethoxy, N-[1-carboxy-2-(4-hydroxyphenyl)ethyl]carbamoylmethoxy, N-(1-carboxy-2-phenylethyl)carbamoylmethoxy, N-(1-carboxy-3-methylbutyl)carbamoylmethoxy, N-(1-carboxy-2-indol-3-ylethyl)carbamoylmethoxy, N-(1-carboxy-2-pyrid-3-ylethyl)carbamoylmethoxy, N-(carboxymethyl)-N-(benzyl)carbamoylmethoxy, N-(1-carboxyethyl)carbamoylmethoxy, 1-[N-(carboxymethyl)carbamoyl]ethoxy, N-(1-carboxy-2-hydroxyethyl)carbamoylmethoxy, N-(1-carboxycycloprop-1-yl)carbamoylmethoxy, N-(1-carboxy-1-methylethyl)carbamoylmethoxy, N-(1-carboxy-2-cyclohexylethyl)

carbamoylmethoxy, N-(1-carboxy-2-methylpropyl) carbamoylmethoxy, N-(1-carboxy-2-imidazol-4-ylethyl) carbamoylmethoxy, N-(1-carboxy-2-(1-methylimidazol-4-yl)ethyl]carbamoylmethoxy, N-(1-carboxy-2-t-butoxypropyl)carbamoylmethoxy, N-(1-carboxy-3-methylthiopropyl)carbamoylmethoxy, N-(1-carboxy-2-methylbutyl)carbamoylmethoxy, N-(1-carboxy-2-imethylpropyl)carbamoylmethoxy, N-(1-carboxy-1-methyl-2-indol-3-ylethyl)carbamoylmethoxy, N-(1-carboxy-2hydroxypropyl)carbamoylmethoxy and N-(1-carboxy-1-cyclohexylmethyl)carbamoylmethoxy and $R^4$ is bromo, methoxy or methylthio or a pharmaceutically acceptable salt thereof.

6. A compound of formula (I) according to claim 1 wherein $R^6$ is hydrogen or a pharmaceutically acceptable salt thereof.

7. A process for preparing a compound of the formula (I) as claimed in claim 1 which comprises:

Process 1):
oxidising a benzothiazepine of formula (II):

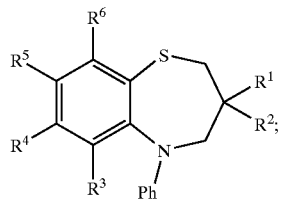

(II)

Process 2):
reacting an alcohol of formula (IIIa) or (IIIb):

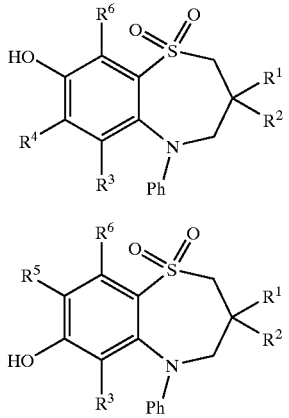

(IIIa)

(IIIb)

with a compound of formula (IV):

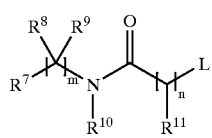

(IV)

wherein L is a displaceable group;

Process 3):
reacting an acid of formula (Va) or (Vb):

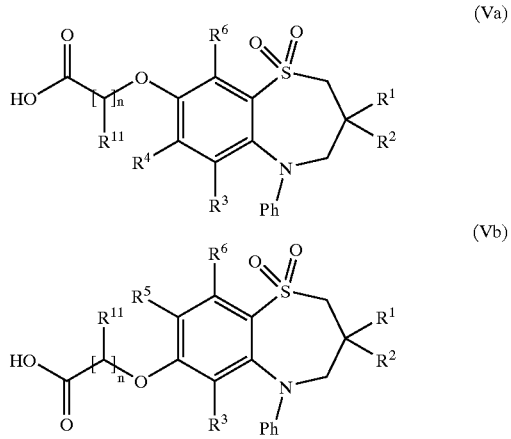

(Va)

(Vb)

or an activated derivative thereof; with an amine of formula (VI):

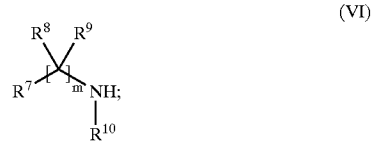

(VI)

Process 4):
for compounds of formula (I) wherein $R^7$ is a group of formula (IB); reacting an acid of formula (VIIa) or (VIIb):

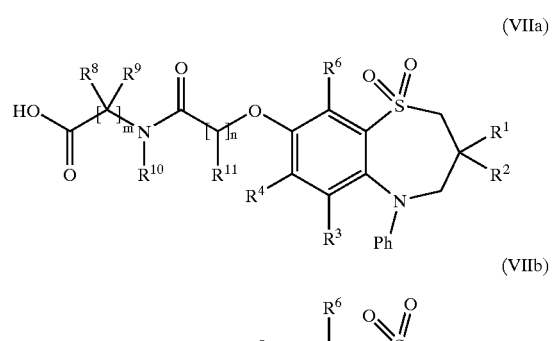

(VIIa)

(VIIb)

or an activated derivative thereof; with an amine of formula (IX):

(VI)

wherein $R^1$, $R^2$, $R^3$, $R^4$, $R^5$, $R^6$, $R^7$, $R^8$, $R^9$, $R^{10}$, $R^{11}$, $R^{12}$ and $R^{13}$, m, n, and p are as defined in claim 1; and optionally:

i) converting a compound of the formula (I) into another compound of the formula (I);
ii) removing any protecting groups;
iii) forming a pharmaceutically acceptable salt.

8. A pharmaceutical composition which comprises a compound of formula (I), or a pharmaceutically acceptable salt thereof, as claimed in any one of claims 1 to 6, in association with a pharmaceutically-acceptable diluent or carrier.

9. A compound of formula (Va), (Vb), (VIIa) or (VIIb):

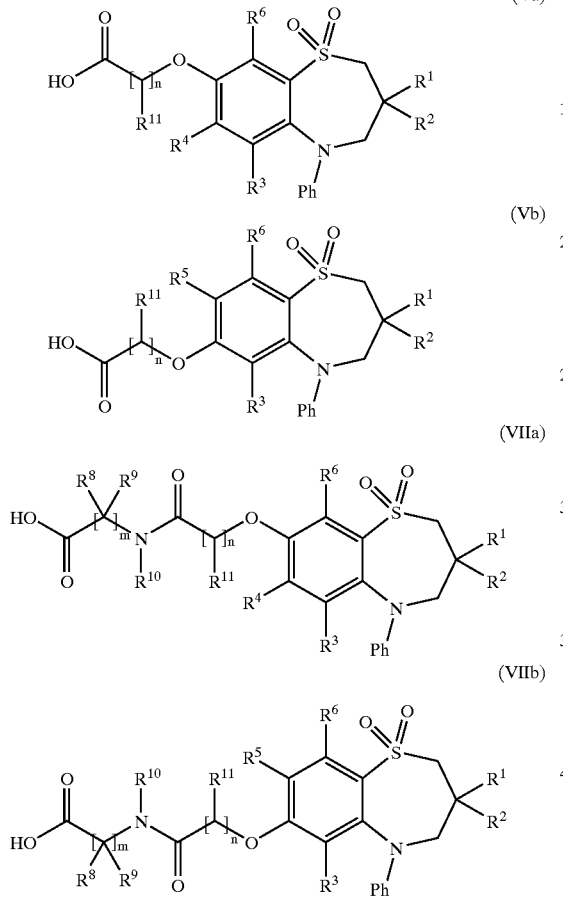

wherein:
$R^1$ and $R^2$ are independently selected from $C_{1-6}$alkyl;
$R^3$, $R^4$, $R^5$ and $R^6$ are independently selected from hydrogen, halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N-($C_{1-4}$alkyl)amino, N,N-($C_{1-4}$alkyl)$_2$ amino, $C_{1-4}$alkanoylamino, N-($C_{1-4}$alkyl)carbamoyl, N,N-($_{1-4}$alkyl)$_2$carbamoyl, $C_{1-4}$alkylS(O)$_a$ wherein a is 0 to 2, $C_{1-4}$alkoxycarbonyl, N-($C_{1-4}$alkyl)sulphamoyl and N,N-($C_{1-4}$alkyl)$_2$sulphamoyl; wherein $R^3$, $R^4$, $R^5$ and $R^6$ may be optionally substituted on carbon by one or more $R^{14}$;
$R^8$ and $R^9$ are independently hydrogen, $C_{1-4}$alkyl or a saturated cyclic group, or $R^8$ and $R^9$ together form $C_{2-6}$alkylene; wherein $R^8$ and $R^9$ or $R^8$ and $R^9$ together may be independently optionally substituted on carbon by one or more substituents selected from $R^{15}$; and wherein if said saturated cyclic group contains an —NH— moiety, that nitrogen may be optionally substituted by one or more $R^{20}$;

$R^{10}$ is hydrogen or $C_{1-4}$alkyl; wherein $R^{10}$ is optionally substituted on carbon by one or more substituents selected from $R^{24}$;
$R^{11}$ is hydrogen, $C_{1-4}$alkyl, carbocyclyl or heterocyclyl; wherein $R^{11}$ is optionally substituted on carbon by one or more substituents selected from $R^{16}$; and wherein if said heterocyclyl contains an —NH— moiety, that nitrogen may be optionally substituted by one or more $R^{21}$;
m is 1–3; wherein the values of $R^8$ and $R^9$ may be the same or different;
n is 1–3; wherein the values of $R^{11}$ may be the same or different;
$R^{14}$ and $R^{16}$ are independently selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N-($C_{1-4}$alkyl)amino, N,N-($C_{1-4}$alkyl)$_2$amino, $C_{1-4}$alkanoylamino, N-($C_{1-4}$alkyl)carbamoyl, N,N-($C_{1-4}$ alkyl)$_2$carbamoyl, $C_{1-4}$alkylS(O)$_a$ wherein a is 0 to 2, $C_{1-4}$alkoxycarbonyl, N-($C_{1-4}$alkyl)sulphamoyl and N,N-($C_{1-4}$alkyl)$_2$sulphamoyl; wherein $R^{14}$ and $R^{16}$ may be independently optionally substituted on carbon by one or more $R^{18}$;
$R^{15}$ is independently selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N-($C_{1-4}$alkyl)amino, N,N-($C_{1-4}$alkyl)$_2$amino, $C_{1-4}$alkanoylamino, N-($C_{1-4}$alkyl)carbamoyl, N,N-($C_{1-4}$ alkyl)$_2$carbamoyl, $C_{1-4}$alkylS(O)$_a$ wherein a is 0 to 2, $C_{1-4}$alkoxycarbonyl, N-($C_{1-4}$alkyl)sulphamoyl and N,N-$C_{1-4}$alkyl)$_2$sulphamoyl, carbocyclyl, heterocyclyl, sulpho, sulphino, amidino, phosphono, —P(O)(OR$^e$)(OR$^f$), —P(O)(OH)(OR$^e$), —P(O)(OH)(R$^e$) or —P(O)(OR$^e$)(R$^f$), wherein R$^e$ and R$^f$ are independently selected from $C_{1-6}$alkyl; wherein $R^{15}$ may be independently optionally substituted on carbon by one or more $R^{19}$; and wherein if said heterocyclyl contains an —NH— moiety, that nitrogen may be optionally substituted by one or more $R^{23}$;
$R^{18}$, $R^{19}$ and $R^{25}$ are independently selected from halo, hydroxy, cyano, carbamoyl, ureido, amino, nitro, carboxy, carbamoyl, mercapto, sulphamoyl, trifluoromethyl, trifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl;
$R^{20}$, $R^{21}$, $R^{23}$ and $R^{26}$ are independently $C_{1-4}$alkyl, $C_{1-4}$alkanoyl, $C_{1-4}$alkylsulphonyl, sulphamoyl, N-($C_{1-4}$ alkyl)sulphamoyl, N,N-($C_{1-4}$alkyl)$_2$sulphamoyl, $C_{1-4}$alkoxycarbonyl, carbamoyl, N-($C_{1-4}$alkyl) carbamoyl, N,N-($C_{1-4}$alkyl)$_2$carbamoyl, benzyl, phenethyl, benzoyl, phenylsulphonyl and phenyl;
$R^{24}$ is selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N-($C_{1-4}$alkyl)amino, N,N-($C_{1-4}$ alkyl)$_2$ amino, $C_{1-4}$alkanoylamino, N-($C_{1-4}$alkyl) carbamoyl, N,N-($C_{1-4}$alkyl)$_2$carbamoyl, $C_{1-4}$alkylS (O)$_a$ wherein a is 0 to 2, $C_{1-4}$alkoxycarbonyl, N-($C_{1-4}$ alkyl)sulphamoyl and N,N-($C_{1-4}$alkyl)$_2$sulphamoyl, carbocyclyl, heterocyclyl; wherein $R^{24}$ may be independently optionally substituted on carbon by one or more $R^{25}$; and wherein if said heterocyclyl contains an —NH— moiety, that nitrogen may be optionally substituted by one or more $R^{26}$;

wherein any saturated cyclic group is a totally or partially saturated, mono or bicyclic ring containing 3–12 atoms of which 0–4 atoms are chosen from nitrogen, sulphur or oxygen, which may be carbon or nitrogen linked;

wherein any heterocyclyl is a saturated, partially saturated or unsaturated, mono or bicyclic ring containing 3–12 atoms of which at least one atom is chosen from nitrogen, sulphur or oxygen, which may be carbon or nitrogen linked, wherein a —CH$_2$— group can optionally be replaced by a —C(O)— or a ring sulphur atom may be optionally oxidised to form the S-oxides; and wherein any carbocyclyl is a saturated, partially saturated or unsaturated, mono or bicyclic carbon ring that contains 3–12 atoms, wherein a —CH$_2$— group can optionally be replaced by a —C(O)—;

or a pharmaceutically acceptable salt thereof.

10. A pharmaceutical composition which comprises a compound of formula (Va), (Vb) (VIIa) or (VIIb), or a pharmaceutically acceptable salt thereof, as claimed in claim 9 in association with a pharmaceutically-acceptable diluent or earner.

11. A method of treating a hyperlipidaemic condition in a warm-blooded animal in need of such treatment, which comprises administering to said animal an effective amount of a compound of formula (I) as defined in any one of claims 1 to 6, or a pharmaceutically acceptable salt thereof.

12. A method of treating a hyperlipidaemic condition in a warm-blooded animal in need of such treatment, which comprises administering to said animal an effective amount of a compound of formula (Va), (Vb), (VIIa) or (VIIb) as defined in claim 9, or a pharmaceutically acceptable salt thereof.

* * * * *